(12) United States Patent
Dalby et al.

(10) Patent No.: US 6,773,920 B1
(45) Date of Patent: Aug. 10, 2004

(54) DELIVERY OF FUNCTIONAL PROTEIN SEQUENCES BY TRANSLOCATING POLYPEPTIDES

(75) Inventors: Brian Dalby, Carlsbad, CA (US); Robert P. Bennett, Encinitas, CA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/937,837

(22) PCT Filed: Mar. 31, 2000

(86) PCT No.: PCT/US00/08571
§ 371 (c)(1),
(2), (4) Date: Jan. 7, 2002

(87) PCT Pub. No.: WO00/58488
PCT Pub. Date: Oct. 5, 2000

Related U.S. Application Data

(60) Provisional application No. 60/127,467, filed on Mar. 31, 1999.

(51) Int. Cl.$^7$ .................. C12N 15/87; C12N 15/67; A61K 38/00
(52) U.S. Cl. .................. 435/462; 435/455; 435/471; 435/468; 530/300; 530/350
(58) Field of Search .................. 435/462, 455, 435/471, 468; 530/300, 350

(56) References Cited

U.S. PATENT DOCUMENTS

| | | | |
|---|---|---|---|
| 4,959,217 A | 9/1990 | Sanders et al. | 424/473 |
| 5,328,984 A | 7/1994 | Pastan et al. | |
| 5,807,746 A | 9/1998 | Lin et al. | 435/375 |
| 6,017,735 A | 1/2000 | O'Hare et al. | 435/69.7 |
| 6,022,950 A | 2/2000 | Murphy | |
| 6,043,339 A | 3/2000 | Lin et al. | |
| 6,287,817 B1 | 9/2001 | Davis et al. | |
| 6,495,518 B1 | 12/2002 | Hawiger et al. | 514/11 |
| 2002/0039765 A1 | 4/2002 | O'Hare et al. | 435/69.7 |
| 2002/0062489 A1 * | 5/2002 | Silver et al. | |
| 2002/0106378 A1 | 8/2002 | O'Hare et al. | 424/186.1 |

FOREIGN PATENT DOCUMENTS

| | | | |
|---|---|---|---|
| EP | 1 118 668 A1 | 7/2001 | ........... C12N/15/62 |
| WO | WO92/15694 | 9/1992 | ........... C12N/15/85 |
| WO | 97/05265 | 2/1997 | ........... C12N/15/87 |
| WO | 98/32866 | 7/1998 | ........... C12N/15/62 |
| WO | 99/05302 | 2/1999 | ........... C12N/15/87 |
| WO | 99/11809 | 3/1999 | ........... C12N/15/87 |
| WO | 99/24559 | 5/1999 | ........... C12N/15/00 |
| WO | 01/49832 | 7/2001 | ............ C12N/9/00 |

OTHER PUBLICATIONS

Zinsser Microbiology, 17th Edition, Joklik et al. eds., Appleton–Century Crofts, New York, pp. 1330–1333.*
NiceProt View of Swiss–Prot: P04637 (available at http://us.expasy.org).*
Phelan A, Elliott G, O'Hare P. Intercellular delivery of functional p53 by the herpesvirus protein VP22. Nat Biotechnol. May 1998;16(5):440–3.*
Lissy NA, Van Dyk LF, Becker–Hapak M, Vocero–Akbani A, Mendler JH, Dowdy SF. TCR antigen–induced cell death occurs from a late G1 phase cell cycle check point. Immunity. Jan. 1998;8(1):57–65.*
Allinquant B, Hantraye P, Mailleux P, Moya K, Bouillot C, Prochiantz A. Downregulation of amyloid precursor protein inhibits neurite outgrowth in vitro. J Cell Biol. Mar. 1995;128(5):919–27.*
Schuler M, Green DR. Mechanisms of p53–dependent apoptosis. Biochem Soc Trans. Nov. 2001;29(Pt 6):684–8.*
Pooga et al. Cell penetrating PNA constructs regulate galanin receptor levels and modify pain transmission in vivo. Nat Biotechnol. Sep. 1998;16(9):857–61.*
Schwarze SR, Hruska KA, Dowdy SF. Protein transduction: unrestricted delivery into all cells? Trends Cell Biol. Jul. 2000;10(7):290–5.*
Kueltzo LA, Middaugh CR. Potential use of non–classical pathways for the transport of macromolecular drugs. Expert Opin Investig Drugs. Sep. 2000;9(9):2039–50.*
Schwarze SR, Dowdy SF. In vivo protein transduction: intracellular delivery of biologically active proteins, compounds and DNA. Trends Pharmacol Sci. Feb. 2000;21(2):45–8.*
Falnes PO, Wesche J, Olsnes S. Ability of the Tat basic domain and VP22 to mediate cell binding, but not membrane translocation of the diphtheria toxin A–fragment. Biochemistry. Apr. 10, 2001;40(14):4349–58.*
Lewin, GENES, Chapter 28, p. 563, John Wiley & Sons New York.*
Bonfanti et al. "p21$^{WAF1}$–derived Peptides Linked to an Internalization Peptide Inhibit Human Cancer Cell Growth," Cancer Research 57: 1442–1446 (1997) American Association for Cancer Research, Baltimore, MD.

(List continued on next page.)

Primary Examiner—Anne-Marie Falk
Assistant Examiner—Daniel M. Sullivan
(74) Attorney, Agent, or Firm—Greenlee, Winner and Sullivan, P.C.

(57) ABSTRACT

The invention provides methods for modulating a cellular process by contacting a cell in culture with a cell process-modifying molecule attached to a translocating polypeptide. For example, in one embodiment, a cell in culture is transfected with a target gene by contacting the cell in culture with a polynucleotide (that contains the target gene) attached to a translocating polypeptide. In another embodiment, expression of a target gene product in a cell in culture that contains a target gene under control of one or more regulatory elements is modulated by contacting the cell in culture with one or more regulatory agents attached to a translocating polypeptide. The one or more regulatory agents are translocated into the cell in culture and interact therein with the one or more regulatory elements to modulate expression of the target gene product by the cell.

37 Claims, 6 Drawing Sheets

OTHER PUBLICATIONS

Chen et al. "A Self–Initiating Eukaryotic Eukaryotic Transient Gene Expression System Based on Cotransfection of Bacteriophage T7 RNA Polymerase and DNA Vectors Containing a T7 Autogene," *Nucleic Acids Research* 22(11):2114–2120 (1994) Oxford University Press.

Elliott and O'Hare. "Intercellular Trafficking of VP22–GFP Fusion Proteins," *Gene Therapy* 6:149–151 (1999) Stockton Press.

Fritz et al. "Gene Transfer into Mammalian Cells Using Histone–Condensed Plasmid DNA," *Human Gene Therapy* 7:1395–1404 (1996).

Invitrogen. "Voyager™–The Power of Translocation," *Invitrogen Catalog* 6(1):6(XP002140132) (1999).

Langel et al. "Cell Penetrating PNA Constructs," *Journal of Neurochemistry* 69(Supp):S260 (1997).

Murphy and Murphy. "Catch VP22: The Hitch–hiker's Ride to Gene Therapy?" *Gene Therapy* 6(1)4–5 (1999).

Niidome et al. "Binding of Cationic α–Helical Peptides to Plasmid DNA and Their Gene Transfer Abilities into Cells," *The Journal of Biological Chemistry* 272(24):15307–15312 (1997).

Prochiantz. "Getting Hydrophilic Compounds into Cells: Lessons from Hemeopeptides," *Current Opinion in Neurobiology* 6(5):629–63 (1996).

Prochiantz. "Peptide Nucleic Acid Smugglers," *Nature Biotechnology* 16:819–820 (1998).

Wen et al. "Identification of a Signal for Rapid Export of Proteins from the Nucleus," *Cell* 82:463–473 (1995), Cell Press.

Zaitsev et al. "H1 and HMG17 Extracted from Calf Thymus Nuclei are Efficient DNA Carriers in Gene Transfer," *Gene Therapy*, 4(6)596–592 (1997) Stockton Press.

Abremski, K. et al. (1983), "Studies on the Properties of P1 Site–Specific Recombination: Evidence for Topologically Unlinked Products following Recombination," Cell 32:1301–1311.

Aints, A. et al. (Nov. 1999), "Intercellular Spread of GFP–VP22," J. Gene Med. 1:275–279.

Bottger, M. et al. (1990), "Transfection by DNA–nuclear protein HMG1 complexes: Raising of efficiency and role of DNA topology," Arch. Geschwulstforsch. 60:265–270.

Cheng, S. et al. (Jun. 1994), "Effective amplification of long targets from cloned inserts and human genomic DNA," Proc. Natl. Acad. Sci. USA 91:5695–5699.

Derer et al. (1999), "Direct protein transfer to terminally differenitated muscle cells," J. Mol. Medicine 77:609–613 (Abstract Only).

Derossi, D. et al. (1994), "The Third Helix of the Antennapedia Homeodomain Translocates through Biological Membranes," J. Biol. Chem. 269(14):10444–10450.

Derossi, D. et al. (1996), "Cell Internalization of the Third Helix of the Antennapedia Homeodomain is Receptor–independent," J. Biol. Chem. 271(30):18188–18193.

Dilber, M.S. et al. (1999), "Intercellular delivery of thymidine kinase prodrug activating enzyme by the herpes simplex virus protein, VP22," Gene Therapy 6:12–21.

Elliott, G. and O'Hare, P. (Aug. 1998), "Herpes Simplex Virus Type 1 Tegument Protein VP22 Induces the Stabilization and Hyperacetylation of Microtubules," J. Virology 72(8):6448–6455.

Elliott, G. and O'Hare, P. (1997), "Intercellular Trafficking and Protein Delivery by a Herpesvirus Structural Protein," Cell 88:223–233.

Fischer, U. et al. (1995), "The HIV–1 Rev Activation Domain in a Nuclear Export Signal That Accesses as Export Pathway Used by Specific Cellular RNAs," Cell 82:475–483.

Frick, I.–M. et al. (May 2002), "Uptake and intracellular transportation of a bacterial surface protein in lymphoid cells," Mol. Microbiol. 44(4):917–934.

Guo, F. et al. (Sep. 1997), "Structure of Cre recombinase complexed with DNA in a site–specific recombination synapse," Nature 389:40–46.

Hall, H. et al. (1996), "Inhibition of FGF–stimulated phosphatidylinositol hydrolysis and neurite outgrowth by a cell–membrane permeable phosphopeptide," Curr. Biol. 6(5):580–587.

Hawiger, J. (1999), "Noninvasive intracellular delivery of functional peptides and proteins," Curr. Opinion in Chem. Biol. 3:89–94.

Hoess, R.H. et al. (1982), "P1 site–specific recombination: Nucleotide sequence of the recombining sites," Proc. Natl. Acad. Sci. USA 79:3398–3402.

Le, Y. et al. (1999), "Nuclear targeting determinants of the phage P1 Cre DNA recombinase," Nucl. Acids Res. 27(24):4703–4709.

Morham, S.G. and Shuman, S. (1992), "Covalent and Non-covalent DNA Binding by Mutants of Vaccinia DNA Topoisomerse I," J. Biol. Chem. 267(22):15984–15992.

Perez, F. et al. (1994), "Rab3A and Rab3B Carboxy–Terminal Peptides Are Both Potent and Specific Inhibitors of Prolactin Release by Rat Cultured Anterior Pituitary Cells," Mol. Endocrinol. 8(9):1278–1287.

Perez, F. et al. (1992), "Antennapedia homeobox as a signal for the cellular internalization and nuclear addressing of a small exogenous peptide," J. Cell Sci. 102:717–722.

Richardson, J.H. et al. (Apr. 1995), "Phenotypic knockout of the high–affinity human interleukin 2 receptor by intracellular single–chain antibodies against the α subunit of the receptor," Proc. Natl. Acad. Sci. USA 92:3137–3141.

Schwartz, J. and Zhang, S. (2000), "Peptide–mediated cellular delivery," Curr. Opinion Mol. Therapeutics 2(2):162–167.

Schwarze, S.R. and Dowdy, S.F. (Feb. 2000), "In vivo protein transduction: intracellular delivery of biologically active proteins, compounds and DNA," TiPS 21:45–48.

Schwarze, S.R. et al. (Jul. 2000), "Protein transduction: unrestricted delivery into all cells?" Trends Cell Biol. 10:290–295.

Sclimenti, C.R. et al. (2001), "Directed evolution of a recombinase for improved genomic integration at a native human sequence," Nucl. Acids Res. 29(24):5044–5051.

Shuman, S. and Moss, B. (1987), "Identification of a vaccinia virus gene encoding a type I DNA topoisomerase," Proc. Natl. Acad. Sci. USA 84:7478–7482.

Troy, C.M. et al. (1996), "Downregulation of Cu/Zn Superoxide Dismutase Leads to Cell Death via the Nitric Oxide–Peroxynitrite Pathway," J. Neurosci. 16(1):253–161.

Wang et al. (1997), "Positive and negative regulation of gene expression in eukaryotic cells with an inducible transcriptional regulator," Gene Therapy 4:432–441.

Wilke, M. et al. (1996), "Efficacy of a peptide–based gene delivery system depends on mitotic activity," Gene Therapy 3:1133–1142.

Wybranietz, W.A. (Nov. 1999), "Quantification of VP22–GFP Spread by Direct Fluorescence in 15 Commonly Used Cell Lines," J. Gene Med. 1:265–274.

Zabner, J. et al. (1995), "Cellular and Molecular Barriers to Gene Transfer by a Cationic Lipid," J. Biol. Chem. 270(32):18997–19007.

Derer, W. (1999), "Direct protein transfer to terminally differentiated muscle cells," J. Mol. Med.77:609–613.

* cited by examiner

DELIVERY OF FUNCTIONAL PROTEIN SEQUENCES BY TRANSLOCATING POLYPEPTIDES

CROSS-REFERENCE TO RELATED APPLICATIONS

This application is a U.S. National Stage application filed under 35 U.S.C. 371 of International Patent Application PCT/US00/08571 filed Mar. 31, 2000 which in turn claims priority to U.S. provisional application No. 60/127,467, filed Mar. 31, 1999.

FIELD OF INVENTION

The present invention relates to methods for translocating polynucleotides and polypeptides between cells. More particularly, the present invention relates to use of translocating proteins to deliver a cell process-modifying molecule into the cell where the cell process-modifying molecule interacts specifically with a responsive target site.

BACKGROUND OF THE INVENTION

Translocating proteins are defined by their ability to cross biological membranes, such as cell membranes. A number of translocating proteins, have been described, including VP22 from Herpes Simplex Virus type 1 (G. Elliot and P. O'Hare, Cell 88, 223–233 (1997)), a fragment of the Antennapedia protein from Drosophila (Antp) (D. Derossi et al., Journal of Biological Chemistry 269, 10444–10450 (1994)), and Protein H from Streptococcus pyogenes (Axcrona et al., Manuscript in preparation (1999)).

Antennapedia is a homeoprotein with a DNA binding domain composed of three alpha helices with a beta-turn separating helix 2 and 3. Experiments have demonstrated that a 16 amino acid peptide corresponding to the third helix, named Antp, can translocate across membranes and accumulate in the cytoplasm and nucleus (Derossi et al, supra). This peptide is internalized at a temperature as low as 4° C., suggesting that endocytosis is not responsible for the internalization of the peptide. In addition, since translocation does not require classical endocytosis, Antp does not travel through the endosomal and lysosomal compartments. Therefore, Antp is resistant to proteolysis and has enhanced activity in most cellular compartments (D. Derossi et al., J Biol Chem 271:18188–18193, 1996).

Recent experiments showing that a reverse helix (i.e. the reverse primary sequence) and a helix composed of D-enantiomers can transverse plasma membranes at 4° C. suggest that internalization of Antp involves the formation of inverted micelles in the phospholipid bilayer, making entry into cells receptor-independent and energy free (H. Hall et al., Current Biol 6:580–587, 1996).

The usefulness of Antp as a vector peptide has been proven successful by genetically fusing Antp to various peptides of interest (F. Perez et al., J Cell Sci 102:717–722, 1992; F. Perez et al., Mol Endocrinol 8:1278–87, 1994; and A. Prochiantz, Curr Opinion Neurob 6:629–634, 1996) or by covalent linkage via cysteine residues (D. Derossi et al., supra). Internalization of peptides as large as 41 amino acids and of charged phosphopeptides (B. Allinquant et al., J Cell Biol 128:919–927, 1995) has been demonstrated in neuronal cells. In each case, the sequences fused to Antp retained their expected biological functions. Furthermore, Antp is the only translocating peptide that has been used to deliver oligonucleotides (up to 45 nucleotides in length) to cells in culture (C. M. Troy et al., J Neuroscience 16 253–61, 1996; G. Elliot et al., J Virol 72:6448–6455, 1998).

Protein H is a surface antigen of the human pathogen Streptococcus pyogenes. Protein H is taken up by B- and T-lymphocytes and translocated to the nucleus. In contrast to other translocating proteins, which appear to have no effect on cellular function, protein H has a cytostatic effect thought to be the result of its association with the nuclear proteins SET and hnRNP A2/B1 (D. Derossi et al., supra). To date, the translocation of Protein H coupled to another molecule has not been demonstrated.

The best studied of the translocating proteins is the Herpes Simplex Virus protein VP22, which has the unique ability to translocate between cultured mammalian cells. When cells are transfected with a plasmid encoding the VP22 protein, the expressed protein accumulates in the cytoplasm of transfected cells and, by translocating across cell membranes, spreads to the surrounding non-transfected cells where it accumulates in the nuclei. This process can occur at 4° C. and also appears to be energy-free and independent of endocytosis. When protein trafficking though the cell is blocked using Brefeldin A, export of VP22 can still occur. Studies of cytoskeletal elements during VP22 trafficking suggest that the actin cytoskeleton may be involved in export or import of VP22 (Elliot and O'Hare, supra).

Delivery of several functional VP22 fusion proteins has been described, including VP22-p53 (A. Phelan et al., Nature Biotechnology 16:440–443, 1998)) and VP22-thymidine kinase (M. S. Dilber et al., Gene Therapy 6:12–21, 1999). At least twenty different mammalian cell types can take up a functional VP22-GFP fusion protein (Elliot and O'Hare, supra; Aints A., et al., J. Gene Med. 1:275–9, 1999; and Wybranietz W. A. et al., J. Gene Med. 1:265–274, 1999), including mouse skeletal myoblasts that are refractory to conventional transfection techniques (Derer W. et al., J. Mol. Med. 77: 609–6138, 1999).

Transfection of cells with plasmid DNA has been an invaluable tool for the study of biological systems. A variety of transfection methods (e.g. lipids, calcium phosphate) exist in the marketplace; however, these methods rarely result in more than 50% of cells expressing a gene carried on a plasmid with which the cells are transfected. Since most cells do take up exogenous DNA, inefficient transfections do not appear to be due to inability of the DNA complex to enter the cell. The majority of DNA is internalized by endocytosis with very little of the internalized DNA ever reaching the cytoplasm or nucleus where expression takes place. Indeed, observations of directly injected lipid-DNA complexes suggest that movement from the endosomes to the cytoplasm and nucleus is the most important limitation to successful transfections (J. H. Richardson et al., Proc. Natl. Acad. Sci.92:3137–3141, 1995). Consistent with this observation, peptides with membrane fusion activity, like the fusogenic peptide of hemagglutinin (J. Zabner et al., Journal of Biological Chemistry 270:18997–9007, 1995), or a nuclear targeting sequence (M. Wilke et al., Gene Therapy 3, 1133–1142 (1996)) can increase transfection efficiencies in some cases.

Thus, there is a need in the art for new and better methods for modulating expression in cells of target genes and for transfection reagents and methods of their use to overcome the major blocks to expression of transfected genes, i.e., degradation in the endosomes and the inability of DNA to enter the cell nucleus.

BRIEF DESCRIPTION OF THE INVENTION

The present invention overcomes these problems in the art by providing method(s) for modulating a cellular process in a cell in culture by contacting such a cell with a cell process-modifying molecule attached to a translocating polypeptide under suitable conditions, whereby the cell process-modifying molecule is translocated into the cells in culture and interacts specifically therein with a target site responsive to the cell process-modifying molecule, thereby modulating a cellular process in the cell.

In another embodiment, the present invention provides method(s) for transfecting a cell in culture with a target gene by contacting the cell under suitable conditions with a polynucleotide comprising the target gene attached to a translocating polypeptide, whereby the cell is transfected with the target gene.

In still another embodiment, the present invention provides method(s) for modulating expression of a target gene product in a cell in culture that is transfected with the target gene under control of one or more regulatory elements by contacting the cell under suitable conditions with one or more regulatory agents attached to a translocating polypeptide, whereby the one or more regulatory agents are translocated into the cell and interact therein with the one or more regulatory elements, thereby modulating expression of the target gene product by the cell.

In yet another embodiment, the present invention provides vector(s) comprising a polynucleotide encoding a cell process-modifying molecule attached to a translocating polypeptide.

BRIEF DESCRIPTION OF THE FIGURES

FIG. 2A shows the ATF-2/LexA DNA binding domain (DBD) fusion protein binds the LexA operator (Op) upstream of the minimal TK promoter and the luciferase reporter gene, but does not activate transcription. FIG. 2B shows that the ATF-2 sFv-VP16 fusion protein binds ATF-2 and activates transcription. FIG. 2C shows that the CREB sFv-VP16 fusion protein does not bind ATF-2 and cannot activate transcription. FIG. 2D shows that the fusion protein composed of VP22, the ATF-2 sFv, and VP16 is delivered to the nucleus, where it binds ATF-2 and activates transcription.

FIG. 3A shows the chemical structure of a phenylboronic acid (PBA)-adapted nucleotide (PBA-dUTP). FIG. 3B shows the chemical structure of a salicylhydroxamic acid (SHA)-adapted amino acid (R=lysine). FIG. 3C shows the reaction of the PBA-adapted nucleotide and the SHA-adapted amino acid to create a bifunctional linker molecule that attaches the oligonucleotide to VP22.

DETAILED DESCRIPTION OF THE INVENTION

In accordance with the present invention, there are provided method(s) for modulating a cellular process by contacting a cell in culture under suitable conditions with a cell process-modifying molecule attached to a translocating polypeptide, whereby the cell process-modifying molecule is translocated into the cell and interacts specifically therein with a target site responsive to the cell process-modifying molecule, thereby modulating a cellular process in the cell.

As used herein, the term "translocating protein" means a protein, polypeptide, or functional fragment thereof, that crosses biological membranes. Translocating proteins, polypeptides, functional fragments and homologues thereof, possess the following properties: resistance to proteolysis, receptor-independent penetration of cell membranes, and substantially energy-free penetration of cell membranes. Exemplary translocating proteins that can be used in the invention methods and constructs include VP22 from Herpes Simplex Virus type 1 (G. Elliot and P. O'Hare, 1997, supra), a fragment of the Antennapedia protein from Drosophila (Antp) (amino acids 43 through 58) (5'-RQIKIWFQNRRMKWKK-3') (SEQ ID NO:21) (Axcrona et al., supra 1999), Protein H from *Streptococcus pyogenes* (D. Derossi et al., *J. Biol. Chem.*, 271:18188–93, (1996)), and the like. While each translocating protein has distinct properties, the general application of translocating proteins is to deliver other molecules to cells, either by constructing a fusion molecule (e.g., a fusion protein) or by attaching the desired molecule to the translocating protein (e.g. covalently or by means of a linker). In fusion proteins the translocating protein can be located either in the N-terminal or the C-terminal position. The preferred fusion protein or polypeptide for use in practice of the invention methods is a VP22 polypeptide.

The term "VP22 polypeptide" is used herein to refer to the herpes viral VP22 protein, as well as to functional fragments thereof, that have the translocating properties of the intact protein. In addition, the term "VP22 polypeptide" as used herein encompasses homologues of VP22 protein, such as those derived from varicella zoster virus (VZV), equine herpesvirus (EHV), bovine herpesvirus (BHV), and the like, and transport-active (i.e. "functional") fragments, mutants and chimeric combinations thereof.

Figure 4:
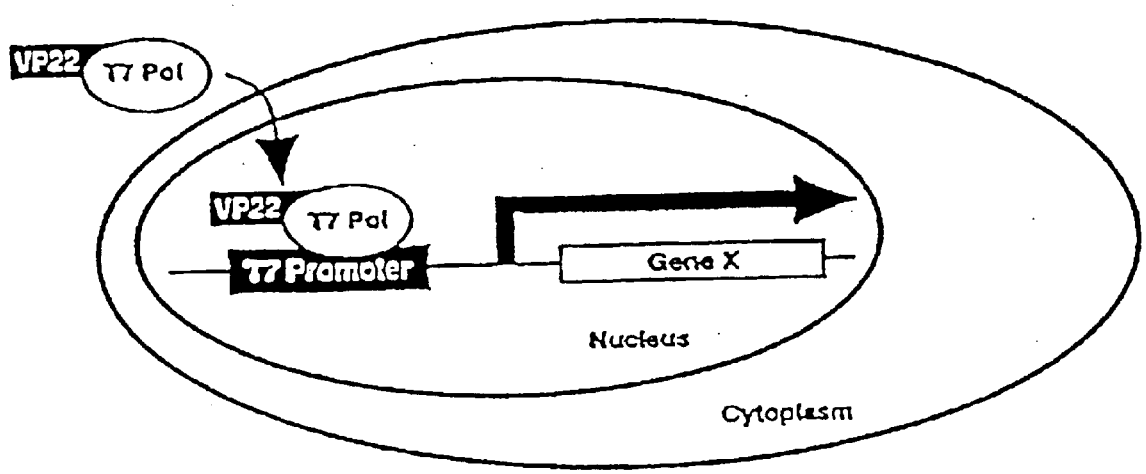
FIG. 4 is a schematic diagram illustrating a VP22-T7 RNA polymerase (T7 pol) expression system. VP22-T7Pol accumulates in the nucleus upon exogenous addition to tissue culture cells. In the nucleus, the VP22-T7 pol fusion protein recognizes the T7 promoter and activates transcription of gene X.

In particular, VP22 polypeptide encompasses polypeptides corresponding to amino acids 60-301 and 159-301 of the full HSV1 VP22 sequence (1-301), whose sequence is disclosed in FIG. 4 in WO 97/05265. Homologous proteins and fragments based on sequences of VP22 protein homologues from other herpes viruses are described in U.S. Pat. No. 6,017,735, which is incorporated herein by reference in its entirety.

The term "fusion protein" as used herein refers to two distinct proteins, polypeptides, peptides, and/or fragments not normally associated with each other in nature that are encoded by the same reading frame, resulting in the two or more distinct proteins and/or fragments being "fused" together. The fusion proteins used in invention methods are produced from nucleotide sequences encoding a translocating polypeptide, e.g., a VP 22 polypeptide, and another functional peptide in the same reading frame. The polynucleotide encoding the fusion protein may also contain in the same reading frame additional peptide or polypeptide sequences useful in the invention methods, such as epitope-tag encoding sequences, affinity purification-tag encoding sequences, additional functional protein encoding sequences, and the like, or a combination of any two or more thereof.

In one embodiment, the invention provides method(s) for transfecting a cell with a target gene by contacting the cell under suitable conditions with a polynucleotide comprising the target gene attached to a translocating polypeptide, whereby the cell is transfected with the target gene. As used herein, the term "transfected" means that a gene translocated into a cell in culture due to the translocating properties of an attached translocating polypeptide is expressed in the cell, at least transiently, i.e., the cell is transiently transfected with the target gene.

The size of polynucleotide that can be transfected into a cell according to the invention methods ranges from about 10 nucleotides to about 10 kilobases (kb). For example, polynucleotides in the range from about 20 nucleotides (nt) to about 5 kb, or from about 100 to 500 nt can be transfected into cells using the invention methods. Generally, the target polynucleotide is transiently transfected into a cell population in culture, for example, in a monolayer or tissue culture. None of the conventional means used to assist transfection or transduction is required, such as electroporation, infection employing viral vectors, calcium phosphate transfection, dextran sulfate transfection, lipofection, cytofection, particle bead bombardnent, and the like. Instead all that is required is contact (i.e., co-culture) of the cell population to be transfected with purified translocation protein or with synthetically prepared translocating protein having a polynucleotide of interest attached thereto by means of a covalent bond or linker molecule, as described herein. Any type of prokaryotic or eukaryotic cell in culture can be transfected using invention methods, for example, mammalian, yeast, insect or plant cells. However, it is presently preferred that the cells in culture be a monolayer of mammalian or insect cells.

In invention methods wherein a translocating protein is attached to plasmid DNA (i.e., via either covalent or non-covalent interactions), the DNA can be delivered to the nucleus for gene expression. Delivery of DNA using translocating proteins as described herein is an extremely valuable research tool. In up to 100% of the cells into which a desired polynucleotide containing an open reading frame (e.g., a polynucleotide contained in a plasmid) is delivered by an invention translocating protein, the polynucleotide is internalized, transported to the nucleus, and the open reading frame is then expressed, thus creating a homogeneous population of cells for studying such cell processes as cell cycle regulation, transcription regulation, translation regulation, and the like.

In another embodiment according to the invention, method(s) are provided for modulating expression of a target gene product in a cell in culture that contains a target gene under control of one or more regulatory elements. In this embodiment, the invention method is practiced by contacting the cell in culture under suitable conditions with one or more regulatory agents attached to a translocating polypeptide, whereby the one or more regulatory agents are translocated into the cell in culture and interact therein with the one or more regulatory elements, thereby modulating expression of the target gene product by the cell.

For example, a polynucleotide attached to a translocating polypeptide, such as VP22, can be translocated into the nucleus of the cell for expression of all or a part of the polynucleotide. In one embodiment, the polynucleotide comprises an open reading frame encoding a protein of interest, such as a target gene product or reporter gene product. Alternatively, the polynucleotide can be a vector (e.g., a supercoiled plasmid) containing a cloned open reading frame that encodes a target gene.

It has been discovered that the translocating protein and attached cell process-modifying molecule can be directed to the cytoplasm for expression as well as to the cell nucleus of the population of cells in culture if the translocating protein is attached (e.g., fused) to a nuclear export signal (NES). Signals for the export of proteins from the nucleus have recently been described. Analysis of PKI (heat stable inhibitor of cAPK, cyclic AMP-dependent protein kinase A) (Y. Wang et al., *Gene Therapy* 4, 432–441 (1997)) and the HIV Rev protein (W. Wen et al., *Cell,* 82, 463–473 (1995)) has revealed a leucine rich sequence that is sufficient to direct heterologous sequences out of the nucleus and into the cytoplasm. Furthermore, fusion of the NES to a heterologous protein that includes the canonical SV40 larger T antigen NLS has been shown to result in the distribution of the protein between the cytoplasmic and nuclear compartments (Wang et al., supra). Similarly, the Rev protein contains sequences for both nuclear import and export and is found in both the cytoplasmic and nuclear compartments of cells (Wen, et al, supra). Thus, incorporation of a NES is a potential method to modulate the nuclear targeting of translocating proteins, such as VP22, especially since the PKI NES can partially counteract the very strong signals of the SV40 NLS. When attached to a nuclear export signal, the translocating polypeptide and any attached polynucleotide can be stably introduced into the cytoplasm as well as the nucleus of the cells in culture, thereby accomplishing partition of the polynucleotide between cellular compartments. In the cytoplasm, regulation of expression of a gene contained in the polynucleotide can be regulated using invention methods as described herein.

Nuclear export signals suitable for use in the practice of the invention are known in the art and include the nuclear export signals derived from the HIV Rev protein or the heat stable inhibitor of cAPK, and the like. In many cases, inclusion of a nuclear export signal into the translocation protein-containing construct can be used to stably integrate a target gene of interest into the genome of the cells in culture.

A cell in culture can be contacted with a translocating protein attached to a cell-modifying molecule according to the present invention by a variety of methods. In the one method, an expression cell population transfected with a polynucleotide encoding the translocating protein fused to the cell-modifying molecule (e.g., as a fusion protein) is mixed and co-cultured with a target cell population that spontaneously takes up the expressed translocation protein with attached cell-modifying molecule. The expressed protein accumulates in the cytoplasm of the transfected expression cells and, by translocating across cell membranes, spreads to the surrounding non-transfected cells where it accumulates in the nuclei. For example, the expression cell can be a prokaryotic cell line, such as *E. coli,* and the target cell line can be any eukaryotic cell line, for example a mammalian cell line, such as CHO or COS, or an insect cell line, such as Drosophila S2, and the like.

Alternatively, the expression cell population can be cultured under conditions that promote expression of a transfected gene, a cell lysate can be prepared of the transfected expression cell population and the lysate can be applied to a cultured target cell population using methods known in the art and as described in the Examples herein. When the translocation protein is VP22, the VP22 or fusion protein containing VP22 will translocate to the nuclei of substantially 100% of the cell population. It is also possible to culture the target cells with purified translocation protein-containing molecules or with synthetically prepared molecules containing the translocating protein attached to a polypeptide or nucleotide by means of a covalent bond or linker, as described herein. The translocating polypeptide and attached molecule will translocate to an entire cell population in culture within about 10 minutes to about 72 hours, more typically within about 10 minutes to about 50 hours; preferably within about 10 minutes to about 24 hours. However, in some cases, no more than about 10 minutes is required for uptake of a translocating polypeptide and attached molecule by an entire cell population.

Fusions of translocating polypeptides with known DNA binding proteins can also be used to deliver DNA containing an open reading frame (e.g., a plasmid) to tissue culture cells. In this embodiment of the invention methods, the DNA binding protein acts as a linker for attaching the translocating protein to the cell-modifying polynucleotide (i.e. a plasmid containing a polynucleotide that acts to modify a cell process). Examples of protein linkers that may be fused to translocating proteins for the delivery of polynucleotides, such as plasmid DNAs, include histone 1 (H1) protein (M. Wilke et al., supra and Niidome, et al., *J. Biol. Chem.* 272, 15307–15312 (1997)) and the non-histone protein HMG-17 (high mobility group 17) (S. V. Zaitsev, et al., *Gene Ther.* 4, 586–592 (1997)). HMG-17 interactions with DNA have been studied in depth and demonstrate that HMG-17 interacts with DNA in a non-cooperative, non-specific, and reversible manner (M. Bottger et al., *Arch. Geschwulstforsch* 60, 265–270 (1990)). In each case, either the entire DNA binding protein, or a functional fragment thereof (i.e. a fragment having DNA binding activity) may be used.

It may be preferred to complex the DNA with a reagent, such as polyethylenimine (PEI), that condenses and neutralizes the charged DNA prior to mixing with the translocating protein, or translocating protein-DNA binding domain fusion.

Alternatively, if a shorter peptide linker is advantageous in the particular system used, the peptide linker may be fused to a translocating protein either as a chemically synthesized peptide or as a nucleotide encoding a fusion protein to be expressed in a prokaryote expression system. Examples of short peptide sequences that may be fused to a translocating protein either as a chemically synthesized peptide or as a fusion protein include polylysine sequences and sequences containing three or more repeats of the peptide sequence LARL, for example, LARL-LARL-LARL (SEQ ID NO:3) (J. D. Fritz et al., *Hum. Gene Ther.* 7:1395–1404 (1996)). In some cases, from three to about 100 repeats of the LARL sequence may be used as a linking peptide as described herein; typically from 3 to about 50 repeats, with 3 up to about 20 repeats being presently preferred.

A preferred linker for attaching a translocating protein to a cell-modifying polynucleotide is the Vaccinia virus topoisomerase I protein, or a mutant form thereof, which allows the formation of stable topoisomerase I-DNA conjugates. Vaccinia DNA topoisomerase, a 314 aa virus-encoded eukaryotic type I topoisomerase (I), binds to duplex DNA and cleaves the phosphodiester backbone of one strand (S. Shuman and B. Moss, *Proc. Natl. Acad. Sci. USA* 84: 7478–7482 (1987)). The enzyme exhibits a high level of sequence specificity, akin to that of a restriction endonuclease. Cleavage occurs at a consensus pentapyrimidine element 5'-(C/T)CCTT-3' in the scissile strand (S. Cheng et al., *Proc. Natl. Acad. Sci. USA* 91: 5695–5699 (1994); J. M. Clark, *Nucleic Acids Res.* 16: 9677–9686 (1988); and S. G. Morham and S. J. Shuman, *Biol. Chem.* 267: 15984–15992 (1992)). In the cleavage reaction, bond energy is conserved via the formation of a covalent adduct between the 3' phosphate of the incised strand and a tyrosyl residue (Tyr-274) of the protein. Vaccinia topoisomerase can religate the covalently held strand across the same bond originally cleaved (as occurs during DNA relaxation) or it can religate to a heterologous acceptor DNA and thereby create a recombinant molecule. When attached to an invention translocating protein, the Vaccinia topoisomerase I linker will attach to a double stranded oligonucleotide having single 5' A base overhangs, such as are created in Taq mediated PCR. Such topoisomerase I-DNA conjugates may then be introduced into cells.

Figure 6:
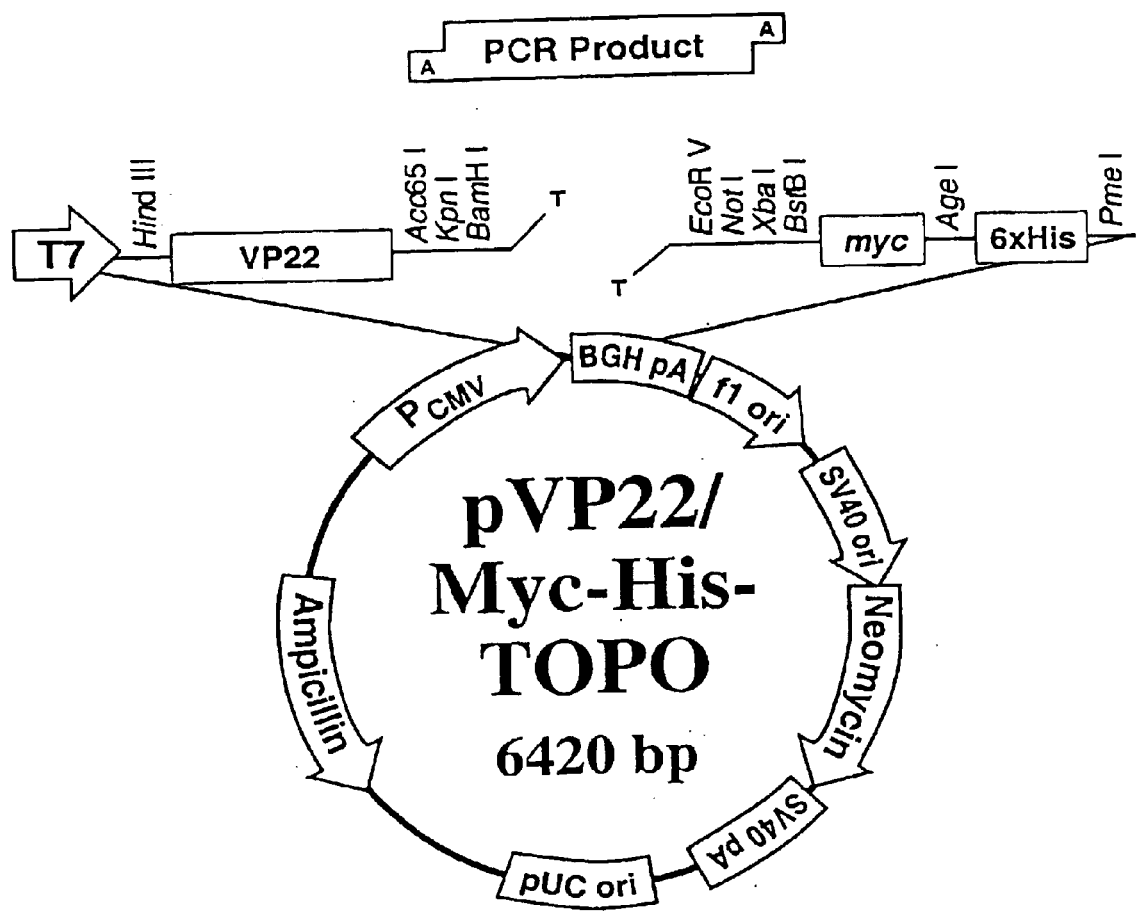
FIG. 6 is a map of pVP22/Myc-His-TOPO® vector, which contains the T7 promoter (T7), VP22 open reading frame (VP22), a multiple cloning site modified by covalent coupling of the Vaccinia Virus Topoisomerase I protein (T) to linearized vector DNA, a myc epitope (myc), and a polyhistidine tag (6xHis). A PCR product with a single 3' A base overhang can be inserted into the topoisomerase-adapted site.

FIG. 6 illustrates a suitable vector wherein Vaccinia topoisomerase I linker is used to attach a translocating protein to a double-stranded oligonucleotide of interest. Vector pVP22/Myc-His TOPO® (SEQ ID NO:2), utilizes Vaccinia topoisomerase I linker to attach VP22 to a double stranded PCR product (i.e., a cell-process modifying oligonucleotide) having single 5' A base overhangs to create a VP22 fusion with vector DNA. Such topoisomerase I-DNA conjugates may then be introduced directly into cells.

In another embodiment, a translocating protein is used to increase the efficiency of plasmid delivery in conjunction with a cationic liposome. Fusion of a translocating protein to a protein domain that readily associates with a cationic liposome, for example a hydrophobic transmembrane domain or a glycosylphosphatidylinositol (GPI) anchor, facilitates interaction at the lipid-DNA interface. Following endocytosis of the liposome-DNA complex, the translocating protein will translocate the complex through the endosomal membrane and into the cell cytoplasm and, eventually, to the nucleus for gene expression. Translocating proteins may also be used to enhance transfection efficiencies in conjunction with compounds, such as chloroquine, that inhibit lysosomal hydrolases (Niidome et al., *J. Biol. Chem.*, 272:15307–12, 1998).

Polynucleotides encoding fusion proteins may be constructed by standard molecular biology techniques (J. Sambrook, E. F. Fritsch and T. Maniatis (1989). *Molecular Cloning, A Laboratory Manual.* Cold Spring Harbor Laboratory Press. Cold Spring Harbor, N.Y.), transfected into tissue culture cells and tested for translocation ability by use of suitable methods, e.g., immunofluorescence, as are known in the art. See also the methods discribed in the Examples herein.

Inducible systems are used to study the phenotypic effects of protein expression. Since inducible systems allow expression of a protein on demand, such systems can be used as a research tool to study cell processes and even to enable the expression of toxic proteins in tissue culture. Current systems for inducible mammalian expression use transcriptional elements from diverse organisms, for example, *E. coli*

(U. Fischer et al., *Cell* 82:475–483 (1995)), or Drosophila (M. Gossen et al., *TIBS* 18:471–475 (1993)) that are constitutively expressed in a cell line along with a vector that contains a promoter responsive to transcriptional regulators. Addition of an effector molecule causes binding of the transcriptional regulators to the inducible promoter, thus turning on gene expression.

The present invention provides a novel approach to this problem by providing method(s) for modulating expression of a target gene product in a mammalian cell transfected with the target gene under control of one or more regulatory elements. In the invention method, the target cell is contacted under suitable conditions with one or more regulatory agents attached to a translocating polypeptide, whereby the one or more regulatory agents are translocated into the mammalian cell and interact therein with the one or more regulatory elements, thereby modulating expression of the target gene product by the cell. The translocating polypeptide used in invention methods for modulating expression of a target gene product can be any of the translocating polypeptides disclosed herein, but is preferably a VP22 polypeptide.

The regulatory agent can be a polynucleotide, a protein or polypeptide, or a small molecule. For example, the regulatory element can be a promoter operatively linked to a target gene wherein translocation of the regulatory agent transactivates expression of the target gene product by the promoter. It is preferred that the regulatory agent be specific for the promoter, such as a polymerase specific for the promoter.

An exemplary inducible system according to the present invention utilizes the RNA polymerase of bacteriophage T7, which has been used to direct gene expression in mammalian cells. Expression of T7 RNA polymerase (T7 RNAP) by Vaccinia virus (A. Ramsey-Ewing and B. Moss, *J. Biol Chem.* 271:16962–16966, 1996; T. R. Fuerst et al., *Proc. Natl. Acad. Sci.* 83:8122–8126, 1986) or in a stable cell line (O. Elroy-Stein and B. Moss, *Proc. Natl. Acad. Sci.* 87:6743–6747, 1990 and A. Lieber et al., *Nucleic Acids Res.* 17:8485–8493, 1989), or introduction of T7 RNAP protein at the time of transfection (X. Chen, et al., *Cancer Gene Ther.* 2:281–289, 1995 and X. Chen et al., *Nucleic Acids Res.* 22:2114–2120, 1994) promotes specific expression of genes that are located downstream of the small T7 promoter. The specificity that T7 RNAP has for the T7 promoter ensures that the desired gene is expressed and that non-specific gene activation does not occur. Expression using T7 RNAP has been reported to be very strong, 6-fold higher than the RSV promoter in one case (A. Lieber et al., *Nucleic Acids Res.* 17:8485–8493, 1989). In addition, gene expression can be directed by T7 polymerase either in the nucleus (Lieber, supra and J. J. Dunn et al., *Gene* 68:259–266, 1988) or the cytoplasm of cells. These characteristics suggested that T7 RNAP can be used to specifically regulate gene expression by the addition of a T7 RNAP/VP22 fusion protein to cells containing a T7 promoter construct. Direct delivery of T7 RNAP using VP22 technology allows specific control of gene expression and minimizes negative effects of delivery to non-target sites. Thus, the methods of the present invention allow for study of the phenotypic effects of protein expression on demand. Due to the specificity of the invention inducible system, the expression of toxic proteins can also be studied in tissue culture. "Toxic proteins," as the term is used herein, refers to proteins that have immediate intrinsic toxic potential for living systems, including those trans-dominant mutations in proteins leading to constituitively active forms of the protein. Thus toxic proteins are distinguished from "pro-drug" type molecules that require modification after expression to release a toxic potential. Non-limiting examples of toxic proteins that can be used in practice of the invention methods are various oncogene products, such as Raf and Ras oncogene products (Reviewed by Avruch et al. *Trends in Biology* 19:279–83, 1994).

Alternatively, the regulatory agent can be a transcription factor specific for the regulatory element so that translocation of the regulatory agent transactivates expression of the target gene product. For example, the translocating protein can be fused to a DNA binding domain, such as that from the Gal4 protein, and to a common transactivation domain, such as VP16 or B42. In this embodiment of the invention, the translocating protein-containing fusion protein will localize to the nucleus and then specifically activate a promoter which contains upstream binding sites for the DNA binding domain incorporated into the fusion protein.

"DNA-binding protein(s)" contemplated for use herein belong to the well-known class of proteins that are able to directly bind DNA and facilitate initiation or repression of transcription. Exemplary DNA-binding proteins contemplated for use herein include transcription control proteins (e.g., transcription factors and the like; see, for example, Conaway and Conaway, *Transcription Mechanisms and Regulation*, Raven Press Series on Molecular and Cellular Biology, Vol. 3, Raven Press, Ltd., New York, N.Y., 1994; T. Boulikas, *Critical Reviews in Eukaryotic Gene Expression*, 4(2&3):117–321, 1994; A. Klug, *Gene* 135:83–92, 1993; W. M. Krajewska, *Int. J. Biochem.*, 24:1885–1898, 1992.)

Transcription factors contemplated for use herein as a source of such DNA binding domains include, e.g., homeobox proteins, zinc finger proteins, hormone receptors, helix-turn-helix proteins, helix-loop-helix proteins, basic-Zip proteins (bZip), β-ribbon factors, and the like. See, for example, S. Harrison, "A Structural Taxonomy of DNA-binding Domains," *Nature*, 353:715–719. Homeobox DNA-binding proteins suitable for use herein include, for example, HOX, STF-1 (Leonard et al., *Mol. Endo.*, 7:1275–1283, 1993), Mat α-2, INV, and the like. See, also, Scott et al. *Biochem. Biophys. Acta*, 989:25–48, 1989. It has been found that a fragment of 76 amino acids (corresponding to amino acids 140–215 described in Leonard et al., 1993) containing the STF-1 homeodomain binds DNA as tightly as wild-type STF-1. Suitable zinc finger DNA-binding proteins for use herein include Zif268, GLI, XFin, and the like. See also, Klug and Rhodes, *Trends Biochem. Sci.*, 12:464, 1987; Jacobs and Michaels, *New Biol.*, 2:583, 1990; and Jacobs, *EMBO J.*, 11:4507–4517, 1992.

The DNA-binding domain(s) used in the invention methods can also be obtained from a member of the steroid/thyroid hormone nuclear receptor superfamily, or be substantially the same as those obtained from a member of the superfamily. The DNA-binding domains of substantially all members of the steroid/thyroid hormone nuclear receptor superfamily are related. Such domains consist of 66–68 amino acid residues, and possess about 20 invariant amino acid residues, including nine cysteines. Members of the superfamily are characterized as proteins which contain these 20 invariant amino acid residues. The highly conserved amino acids of the DNA-binding domain of members of the superfamily are as follows:

Cys-X-X-Cys-X-X-Asp-X-Ala*-X-Gly*-    (SEQ ID NO:4)

X-Tyr*-X-X-X-X-Cys-X-X-Cys-Lys*-X-

Phe-Phe-X-Arg*-X-X-X-X-(X-X-)Cys-

X-X-X-X-X-(X-X-X-)Cys-X-X-X-Lys-X-

X-Arg-X-X-Cys-X-X-Cys-Arg*-X-X-

Lys*-Cys-X-X-X-Gly*-Met;

wherein X designates non-conserved amino acids within the DNA-binding domain; an asterisk denotes the amino acid residues which are almost universally conserved, but for which variations have been found in some identified hormone receptors; and the residues enclosed in parenthesis are optional residues (thus, the DNA-binding domain is a minimum of 66 amino acids in length, but can contain several additional residues). Such DNA binding domains bind to 2-half site recognition sites, as is well known in the art to transactivate transcription under control of a response element comprising the recognition site.

The GAL4 DNA binding domain does not interact with a 2-half site DNA recognition site. The DNA binding domain of the yeast GAL4 protein comprises at least the first 74 amino terminal amino acids thereof (see, for example, Keegan et al., *Science* 231:699–704, 1986). Preferably, the first 90 or more amino terminal amino acids of the GAL4 protein will be used, for example, the 147 amino terminal amino acid residues of yeast GAL4.

Another DNA binding domain that can be used in the practice of the present invention is the Tet operon. The tetracycline inducible system is well-known in the art (see, e.g., Gossen et al., *Proc. Natl. Acad. Sci.* 89:5547–5551 (1992); Gossen et al., *TIBS* 18:471–475 (1993); Furth et al., *Proc. Natl. Acad Sci.* 91:9302–9306, (1994); and Shockett et al., *Proc. Natl. Acad Sci.* 92:6522–6526 (1995)).

Transcription modulating domains are of two types, those that activate transcription of a gene sequence operatively associated with a response element that is responsive to the invention system (i.e., transcription activation domains) and those that repress or de-activate transcription of a gene sequence operatively associated with a response element that is responsive to the invention system (i.e., transcription repression domains). The ability of the invention system to activate transcription of such a target gene is generally enhanced when the transcription modulating domain attached to the translocating protein is a transcription activation domain. Transcription activation domains contemplated for use in the practice of the present invention can be obtained from a variety of sources and are well known in the art.

Such transcription activation domains are typically derived from transcription factors and comprise a contiguous sequence that functions to activate gene expression when associated with a suitable DNA-binding domain. For example, suitable activation domains can be obtained from the N-terminal region of members of the steroid/thyroid hormone nuclear receptor superfamily, from transcription factor activation domains, such as, for example, VP16, GAL4, NF-kB or BP64 activation domains, and the like (See, for example, M. Manteuffel-Cymborowska, *Acta Biochim Pol.* 46(1):77–89 (1999); T. Tagami et al, *Biochem Biophys Res. Commun.* 232(2):358–63 (1998), W. Westin, *Adv Pharmacol,* 47:89–112 (2000)). The activation domain presently preferred for use in the practice of the present invention is obtained from the C-terminal region of the VP16 protein.

Transcription repressor domains that can be used in the invention methods include those that repress transactivation of gene expression. Exemplary transcription repressor domains suitable for use as the transcription modulating domain in the invention methods include RAFT, CREM, MECP-2, SMRT, NcoR, mSin3A, RAR, TR, SMRTR, and the like.

Another way in which translocating proteins may be used in inducible expression systems for modulating expression of a target gene is to create gene fusions or in vitro covalent linkage with site-specific recombination sequences, which are sequences of nucleic acids that are specifically recognized by a particular site-specific recombinase. Site specific recombinases, as the term is used herein, are enzymes that catalyze the excision and/or recombination of nucleic acid sequences, and may form intermediate complexes with the transfer sequence DNA during the recombination event. These enzymes recognize a relatively short, unique nucleic acid sequence that serves as a site for both recognition and recombination. Recombinases particularly useful in the practice of the invention are those that function in a wide variety of cell types because such enzymes do not require any host specific factors and do not require ATP to function.

Two major families of site-specific recombinases from bacteria and unicellular yeast have been described: the integrase family and the resolvase/invertase family. In these recombinases, strand exchange catalyzed by site specific recombinases occurs in two steps of (1) cleavage and (2) rejoining, involving a covalent protein-DNA intermediate formed between the recombinase enzyme and the DNA strand(s). The nature of the catalytic amino acid residue of the enzyme and the line of entry of the nucleophile is different for these two recombinase families. For cleavage catalyzed by the invertase/resolvase family, the nucleophile hydroxyl is derived from a serine and the leaving group is the 3'-OH of the deoxyribose. For the integrase family, the catalytic residue is a tyrosine and the leaving group is the 5'-OH. In both recombinase families, the rejoining step is the reverse of the cleavage step.

The recombinase activity of Cre has been studied as a model system for the integrases. Cre is a 38 kD protein isolated from bacteriophage P1. It catalyzes recombination at a 34 base pair stretch of nucleic acids called loxP. The loxP site has the sequence 5'-ATAACTTCGTATA GCATACATTATACGAAGTTAT-3' (SEQ ID NO: 5; spacer region underlined), consisting of two 13 base pair palindromic repeats flanking an eight basepair core sequence (Hoess et al., *Proc. Natl. Acad. Sci USA* 79:3398, 1982 and U.S. Pat. No. 4,959,217, the disclosure of which is incorporated herein by reference in its entirety). The repeat sequences act as Cre binding sites with the crossover point occurring in the internal spacer core. Each repeat appears to bind one protein molecule wherein the DNA substrate (one strand) is cleaved and a protein-DNA intermediate is formed having a 3'-phosphotyrosine linkage between Cre and the cleaved DNA strand. Crystallography and other studies suggest that four proteins and two loxP sites (each on a different DNA molecule) form a synapsed structure in which the DNA resembles models of four-way Holliday-junction intermediates, followed by the exchange of a second set of strands to resolve the intermediate into recombinant products (see, Guo, et al., *Nature* 389:40–46, 1997). The asymmetry of the core region of the loxP recombination sequence is responsible for directionality of the recombination reaction. When two loxP sites on the same DNA molecule are in a directly repeated orientation, Cre excises the DNA between these two sites, leaving a single loxP site on the DNA molecule (Abremski et al., *Cell* 32:1301, 1983). Thus, the repeat sequences act as Cre-specific binding sites with the recombination crossover point occurring in the core.

The loxP site is so complex in size that it occurs only in the P1 phage genome. Therefore, use of the loxP sites in the invention methods assures that the enzyme will not cut the transfer sequence within the interior of the sequence unless the transfer sequence is from the P1 phage genome. The activity of Cre in a wide variety of cellular backgrounds, including yeast, shows that Cre does not require host specific factors for activity (Sauer *Mol. Cell. Biol.* 7:2087–2096, 1987) in plant (Albert et al., *Plant J.* 7:649–659, 1995; Dale and Ow, *Gene* 91:79–85, 1990; Odell et al., *Mol. Gen. Genet.* 223:369–378, 1990), or mammalian cells, including both rodent and human cells (van Deursen et al., *Proc. Natl. Acad. Sci. USA* 92:7376–7380, 1995; Agah et al., *J. Clin. Invest.* 100:169–179, 1997; Sauer and Henderson, *New Biologist* 2:441–449, 1990).

The Cre protein also recognizes a number of variant or mutant lox sites (variant relative to the loxP sequence), including the loxB, loxL and loxR sites, which are found in the *E. coli* chromosome. Other variant lox sites include loxP511 (5'-ATAACTTCGTATA GTATACATTATACGAAGTTAT-3' (SEQ ID NO:6; spacer region underlined); loxC2 (5'-ACAACTTCGTATA ATGTATGCTATACGAAGTTAT-3' (SEQ ID NO:7; spacer region underlined; U.S. Pat. No. 4,959,217). Additional variants of the loxP site can be prepared by those of skill in the art and will generally have no more than a total of one to three point mutations in the two repeats that comprise the site-specific recombination sequence. Cre catalyzes the cleavage of the lox site within the spacer region and creates a six base-pair staggered cut. The two 13 bp inverted repeat domains of the lox site represent binding sites for the Cre protein. The two lox sites may differ so long as Cre is able to recognize both lox sites. However, if two lox sites differ in their spacer regions in such a manner that the overhanging ends of the cleaved DNA cannot reanneal with one another, Cre cannot efficiently catalyze a recombination event using the two different lox sites. The efficiency of the recombination event will depend on the degree and the location of the variations in the binding sites. For example, the loxC2 site can be efficiently recombined with the loxP site because the two lox sites differ by a single nucleotide in the left-binding site. Thus, when Cre is the site specific recombinase used in the practice of the invention methods, the site-specific recombination sequence is a loxP site, or a variant thereof recognized by the Cre enzyme.

A recombinase of the integrase family with similar function is Flp, a recombinase identified in strains of *Saccharomyces cerevisiae* that contain 2μ-circle DNA. Flp recognizes a DNA sequence consisting of two 13 basepair inverted repeats flanking an 8 basepair core sequence (5'-GAAGTTCCTATTCTCTAGAAAGTATAGGAACTTC-3' (SEQ ID NO: 8); spacer underlined) called FRT (Flp Recombination Target site). A third repeat follows at the 3' end in the natural sequence, but does not appear to be required for recombinase activity. The Flp gene has been cloned and expressed in *E coli* and in mammalian cells (PCT International Patent Application PCT/US92/01899, Publication No: WO 92/15694, the disclosure of which is herein incorporated by reference) and has been purified (Meyer-Lean et al., *Nucleic Acids Res.* 15:6469, 1987; Babineau et al., *J. Biol. Chem.* 260:12313, 1985; Gronostajski and Sadowski, *J. Biol. Chem.* 260:12328, 1985).

Like Cre, Flp is functional in a wide variety of systems including bacteria (Huang et al., *J. Bacteriology* 179:6076–6083, 1997), insects (Golic and Lindquist, *Cell* 59:499–509, 1989; Golic and Golic, *Genetics* 144:1693–1711, 1996), plants (Lyznik et al., *Nucleic Acids Res* 21:969–975, 1993) and mammals (U.S. Pat. Nos. 5,677,177 and 5,654,182), which shows the Flp does not require host specific factors for operability.

Additional integrases that can be used in practice of invention methods are retroviral integrases, including HIV and ASV integrases (Reviewed in Annu. Rev. Microbiol. 53:245–81, 1990).

Figure 1:
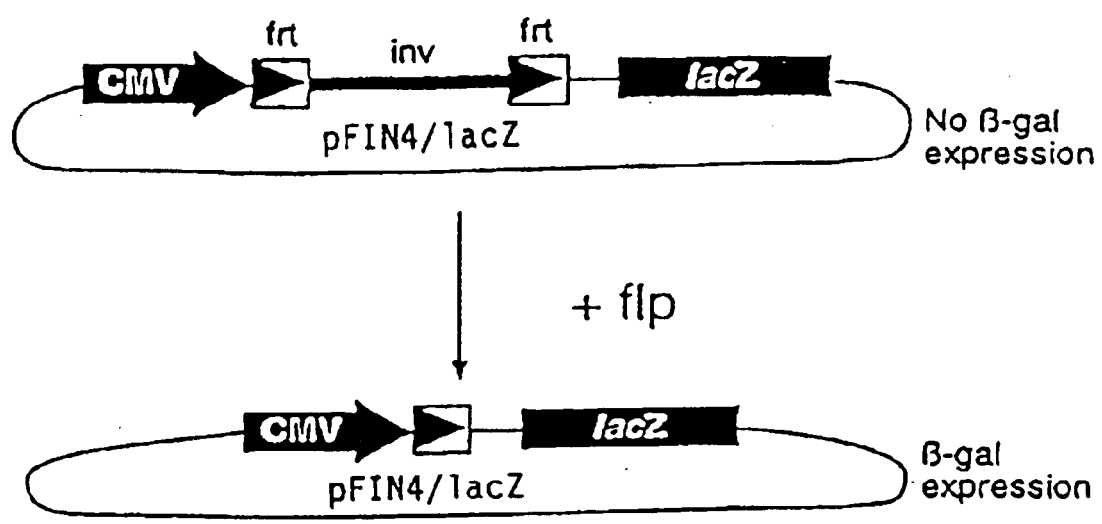
FIG. 1 is a schematic drawing showing pFIN4/lacZ, which has an intervening sequence (inv) flanked by Flp recognition sites (frt) separating the CMV promoter and β-galactosidase gene (lacZ). Interaction of Flp recombinase with pFIN4 results in the removal of the inv sequence and expression of β-galactosidase.
Figure 2A:
FIGS. 2A–D are schematic representations of the process by which a fusion protein composed of VP22, an anti-ATF-2 single chain antibody (sFv), and VP16 is delivered to the nucleus of a cell where it binds ATF-2 and activates transcription.
Figure 2B:
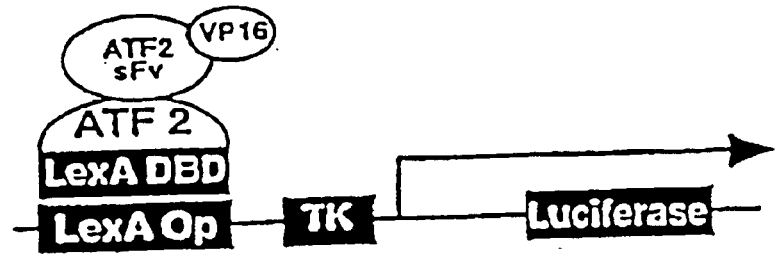
Figure 2C:
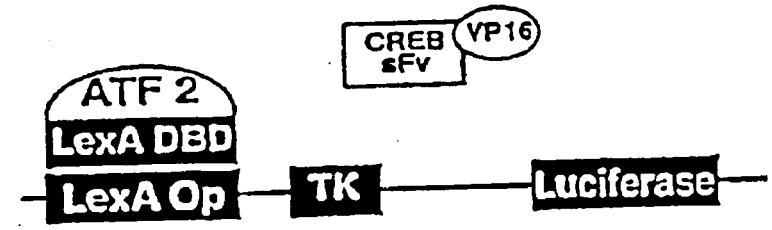
Figure 2D:
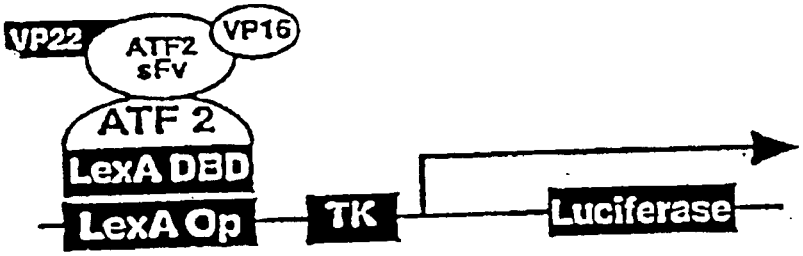

In practice of invention methods for modulating expression of a target gene produce, a site-specific DNA recombinase or integrase fused to a translocating protein may be introduced as described herein into cells that have been transfected with a plasmid containing a transcription-blocking sequence (e.g., a transcription termination sequence) flanked by recombinase recombination sites specific for the recombinase or integrase used and placed between a promoter and an open reading frame encoding a target gene. For example, if the recombinase is Flp, the recombinase sites are frt sites, and if the recombinase is Cre, the recombinase sites are lox sites. Exposure of the transfected cell to the recombinase or integrase-adapted translocating protein results in removal of the transcriptional terminator by the activity of the recombinase and expression of the gene of interest as illustrated in FIG. 1.

Thus, in the invention methods for modulating a cellular process, the one or more regulatory elements can include a transcription-blocking sequence flanked by recombinase recombination sites and the regulatory agent can be a recombinase specific for the recombination sites, wherein translocation of the recombinase causes recombination of the recombination sites, thereby modulating expression of the target gene product.

Alternatively, rather than placing a pair of recombinase sites flanking a polynucleotide segment to be excised, a single recombinase site can be incorporated into (or exist naturally in) the genome of the target cell that also contains a plasmid containing a target gene and a second recombinase site that pairs with the genomic recombinase site. When such a cell is contacted by a recombinase (e.g. integrase) specific for the recombinase site(s) in the target cell, translocation of the recombinase will trigger a recombination event such that the target gene will become stably incorporated into the genome of the target cell at the genomic recombinase site.

The recombinase or integrase may be introduced by mixing of two cell populations, one expressing the translocating protein-enzyme (e.g., Flp or Cre) fusion and the other containing the heterologous gene. Alternatively, the translocating protein-enzyme fusion may be produced in a prokaryotic or eukaryotic expression system, purified using known methods and as described herein, and applied to cells containing the heterologous gene. The cells may be either transiently transfected with the heterologous gene or carry it stably integrated in their genomes.

Alternatively, the regulatory agent used in invention methods for modulating gene expression can be the HIV Rev protein paired with the Rev regulatory element as regulatory element (RRE). As illustrated in Example 5 herein, increasing amounts of Rev protein delivered to target cells containing RRE result in increased expression of an operatively linked target gene.

In another embodiment of the invention method for modifying a cellular process, the protein molecule fused to a translocating protein is a Fv antibody fragment or a single chain antibody (sFv). Preferably polynucleotide encoding a fusion protein containing the translocating protein and sFv is introduced into cells in culture, as described herein, for translocation to the cell nucleus and intracellular expression. If the sFv is specific for an antigen target associated with intracellular machinery involved in a cellular function, for example, a target located within the cell nucleus, binding of the sFv to the intracellular target can interfere with cellular functions, such as Ras signaling (O. Elroy-Stein, T. R. Fuerst, B. Moss, *Proc. Natl. Acad. Sci.* 86, 6126–6130 (1989), membrane transport (O. Cachet, et al., *Cancer Research* 58, 1170–1176 (1998)), or viral replication (J. H. Richardson, J. G. Sodroski, T. A. Waldmann, W. A. Marasco, *Proc. Natl. Acad. Sci.* 92, 3137–3141 (1995)). Additional exemplary intracellular targets for which single chain antibodies can be constructed and used in the invention methods to modify cellular processes include human kinases, transcription factors, proteins controlling apoptosis, cell cycle regulators, oncoproteins, and the like.

Therefore, the one or more regulatory agents used in the invention method(s) for regulating cell processes can include a Fv or sFv specific for a component of the one or more regulatory elements within the cells in culture (whether the regulatory element is native or transfected into the cells), wherein translocation of the Fv or sFv into the cell by the translocating protein and binding of the antibody to the component modulates expression of the target gene product.

For example, intracellular processes have been modified by creating a fusion protein containing an anti-ATF-2 sFv fused to VP22 and the translocational activation domain of VP16 (FIGS. 2A–D). ATF-2 belongs to the bZIP family of transcription factors and controls gene expression via 8-bp ATF/CREB motifs, either as a homodimer or as a heterodimer—for instance, with Jun (S. Huguier et al., *Molecular and Cellular Biology* 18:7020–7029, 1998). If the fusion protein is expressed within a reporter cell line that has ATF-2 bound upstream of a reporter gene, e.g., the bacterial luciferase gene, binding of the sFv in the fusion protein to the ATF-2 antigen in the cell nucleus (FIGS. 2A–D) triggers expression of the ATF-2 sFv-VP16 fusion (FIG. 2B), but not a CREB sFv-VP 16 fusion (FIG. 2C), resulting in expression of the reporter gene. This experiment demonstrates that the ATF-2 sFv is delivered to the cell nucleus where it binds the ATF-2 antigen.

"Fv" as used herein means a genetically engineered fragment containing the variable region of the light chain and the variable region of the heavy chain expressed as two chains but chemically linked; "sFv" as used herein means a genetically engineered molecule containing the variable region of the light chain and the variable region of the heavy chain, linked by a suitable polypeptide linker as a genetically fused single chain molecule.

The linkage of light chain and heavy chain variable regions in a Fv may be noncovalent, as described in Inbar et al., *Proc. Nat'l Acad. Sci. USA* 69:2659–62, 1972. Alternatively, the variable chains can be linked by an intermolecular disulfide bond or cross-linked by chemicals such as glutaraldehyde.

Exemplary linkers used to attach two segments of a Fv or to attach any other two proteins to (e.g., a translocating protein and a DNA binding protein) can be a bifunctional cleavable cross-linker, such as N-succinimidyl(4-iodoacetyl)-aminobenzoate; sulfosuccinimydil(4-iodoacetyl)-aminobenzoate; 4-succinimidyl-oxycarbonyl-α-(2-pyridyldithio)toluene; sulfosuccinimidyl-6-[α-methyl-α-(pyridyldithiol)-toluamido]hexanoate; N-succinimidyl-3-(-2-pyridyldithio)-proprionate; succinimidyl 6[3(-(-2-pyridyldithio)-proprionamido]hexanoate; sulfosuccinimidyl 6[3(-(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine, and the like. Further bifunctional linking compounds are disclosed in U.S. Pat. Nos. 5,349,066, 5,618,528, 4,569,789, 4,952,394, and 5,137,877, each of which is incorporated herein by reference in its entirety.

These linkers can be attached to purified proteins using numerous protocols known in the art, such as those described in Examples 1 and 2 (see Pierce Chemicals "Solutions, Cross-linking of Proteins: Basic Concepts and Strategies," Seminar #12, Rockford, Ill.).

Preferably the antibodies used in the invention methods are sFv, comprising $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, *Methods*, 2: 97–105, 1991; Bird et al., *Science* 242:423–426, 1988; Pack et al., *Bio/Technology* 11:1271–77, 1993; and Ladner et al., U.S. Pat. No. 4,946,778, which is hereby incorporated by reference in its entirety. Such well known procedures can be modified to create fusion proteins comprising a sFv and a translocating protein, as described herein.

For example, the linker in the sFv can be a peptide having from about 2 to about 60 amino acid residues, typically from about 5 to about 40, preferably from about 10 to about 30 amino acid residues. This alternative is particularly advantageous when the ligand moiety is proteinaceous. For example, the linker moiety can be a flexible spacer amino acid sequence, such as those known in single-chain antibody research. Examples of such known linker moieties include GGGGS (SEQ D NO:9), $(GGGGS)_n$ (SEQ. ID NO:10), GKSSGSGSESKS (SEQ ID NO:11), GSTSGSGKSSEGKG (SEQ. ID NO:12), GSTSGSGKSSEGSGSTKG (SEQ ID NO:13), GSTSGSGKSSEGKG (SEQ ID NO:14), GSTSGS-GKPGSGEGSTKG (SEQ ID NO:15), EGKSSGSG-SESKEF (SEQ ID NO:16), SRSSG (SEQ. ID NO:17), SGSSC (SEQ ID NO:18), and the like. A Diphtheria toxin trypsin sensitive linker having the sequence MGRSGGGCAGNRVGSSLSCGGLNLQAM (SEQ ID NO:19) is also useful. Alternatively, the peptide linker moiety can be VM or AM, or have the structure described by the formula: $AM(G_{2\ to\ 4}S)_X AM$ wherein X is an integer from 1 to 11 (SEQ ID NO:20). Additional linking moieties are described, for example, in Huston et al., *PNAS* 85:5879–5883, 1988; Whitlow, M., et al., *Protein Engineering* 6:989–995, 1993; Newton et al., *Biochemistry* 35:545–553, 1996; A. J. Cumber et al., *Bioconj. Chem.* 3:397–401, 1992; Ladurner et al., *J. Mol. Biol.* 273:330–337, 1997; and U.S. Pat. No. 4,894,443, the latter of which is incorporated herein by reference in its entirety.

It is contemplated to be within the scope of the present invention that the target gene within a cell in culture can be a reporter gene, such as is known in the art, for example, a non-endogenous gene encoding a detectable marker, such as the *E. coli* β-galactosidase gene, luciferase, or CAT.

As an aid in purify the fusion molecules or detecting expression triggered by use of the invention methods, it is often convenient to include in the polynucleotide that encodes the reporter gene an additional nucleotide sequence that encodes a protein tag, such as an antibody epitope (e.g., derived from Myc), a fluorescent peptide, or a poly His tag.

A variety of methods can be used for attaching a peptide or oligonucleotide molecule to a translocating protein. For example, the translocating protein can be covalently conjugated to a translocating protein or to a polynucleotide encoding a translocating polypeptide for use in the invention methods using two low molecular weight chemical affinity ligands that can be attached to macromolecules like DNA and to proteins and which combine to form a linker useful in preparation of fusion proteins or fusion genes used in the invention methods. Two such low molecular weight chemical affinity ligands are salicylhydroxamic acid (SHA) and phenylboronic acid (PBA), which quickly react to form a reversible pH-sensitive covalent bond (FIGS. 3A–C), thus providing a convenient linker to attach a translocating protein to another protein or to a polynucleotide. For example, nucleic acid molecules containing PBA can be synthesized using PBA-NTPs (available from ProLinx, Seattle, Wash.) or, if double stranded, can be labeled with PBA-ATP using the enzyme terminal transferase. SHA-NHS ester can also be used to attach SHA to lysine residues present in a translocating protein. In this embodiment, a PBA-adapted molecule and a SHA-adapted translocating protein are covalently linked and applied to cells. Alternatively, other linkers, such as disulfide bonds (which would be disrupted upon delivery to the cytoplasm) or bifunctional linker molecules (e.g., as disclosed herein) may also be used. Covalent linking using these or other linkers known in the art and disclosed herein provides a relatively stable attachment of the translocating protein to another molecule.

In addition, a number of strong non-covalent molecular interactions can be used to generate translocating protein-containing complexes. For example, Strepavidin binds biotin very strongly (the disassociation constant is approximately $10^{-15}$). This strong affinity, which is routinely used to attach proteins to substrates, can be used to form a linker that attaches a cell process-modifying molecule to a translocating polypeptide. For example, a fusion protein containing VP22 translocating protein and strepavidin may be generated and complexed with a biotinylated oligonucleotide to form a linker attaching a cell process-modifying polynucleotide to a translocating polypeptide. Strepavidin binds biotin as a tetramer (tetramer MW=60,000 daltons) and VP22 is believed to act as a multimer, making this combination a suitable one.

Another polypeptide molecule that may be used as a linker to attach a cell process-modifying molecule to a translocating polypeptide for use in invention methods is the single stranded DNA binding protein (SSB) from *E coli*. Only 21 amino-acid residues (amino acid residues 2 through 22) of SSB appear to be involved in binding to ssDNA (i.e., "the functional fragment of SSB"). Furthermore, binding of SSB to ssDNA is not sequence specific. Therefore, a fusion protein containing a translocation protein fused to a functional fragment of SSB is an extremely attractive linker for attaching a translocating protein to an oligonucleotide or to plasmid DNA. Unlike the linking molecules described above (i.e., those containing PBA and SHA or strepavidin and biotin), which require modification of the oligonucleotide to be linked to the translocating protein, fusion proteins containing a SSB and a translocating protein can be attached to unmodified DNAs, thus providing time and cost-saving advantages.

The invention will now be described in greater detail by reference to the following non-limiting examples.

EXAMPLE 1

Introduction of VP22 Fusion Protein into Cells in Culture by Transfection

Figure 5:
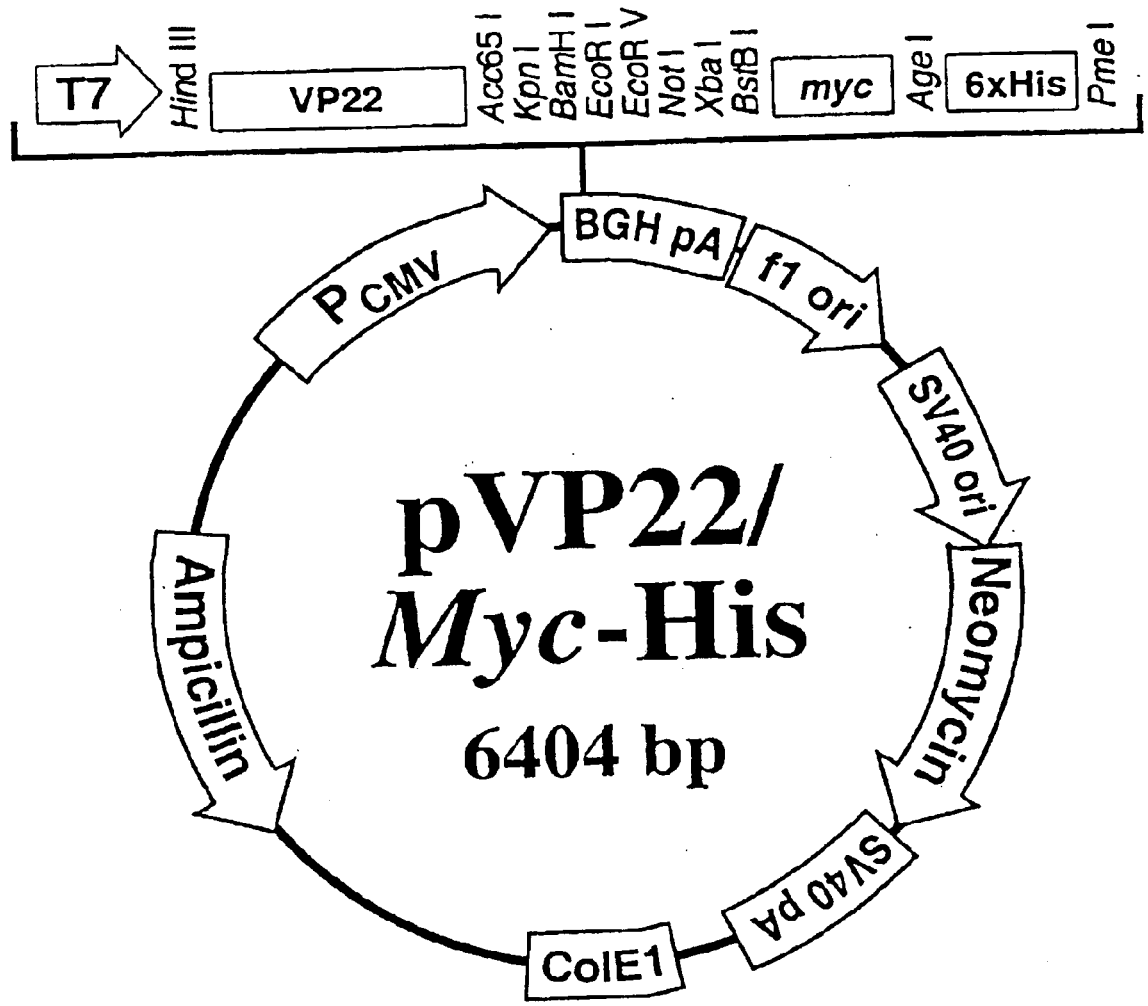
FIG. 5 is a map of vector pVP22/Myc-His, which contains the T7 promoter (T7), VP22 open reading frame (VP22), a multiple cloning site, a myc epitope (myc), and a polyhistidine tag (6xHis).

The complete open reading frame (ORF) encoding the VP22 protein was cloned into the eukaryotic expression vector pcDNA3.1/myc-His (Invitrogen, San Diego, Calif.), to create the vector pVP22/Myc-His (FIG. 5; SEQ ID NO:1), in which the ORF of the fusion partner can be inserted into a multiple cloning site located between the VP22 ORF and sequences encoding the C-terminal Anti-myc epitope and a poly His tag. The anti-myc epitope provides for easy detection of recombinant protein with Anti-myc antibody, and the poly His tag is useful for purification. Alternatively, the vector used was modified by covalent coupling of the Vaccinia Virus Topoisomerase I protein to linearized vector DNA (e.g., pVP22 TOPO® TA Cloning® Kit (Invitrogen)). In this type of vector, the ORF of a gene product of interest (i.e., a "fusion partner") was cloned as a PCR product into the vector. An example of such a Topoisomerase-adapted vector encoding the VP22 polypeptide is pVP22/Myc-His TOPO® vector (FIG. 6; SEQ ID NO:2). In either case, the plasmid containing the VP22 gene fusion was then transfected into cells in culture.

In a typical transfection, COS or CHO cells were seeded into 6 well plates and grown to approximately 50% confluence prior to transfection. For each well, 5 µg DNA was diluted into 1.5 ml OptiMEM medium (Gibco BRL, Chagrin Falls, Ohio) and mixed with 15 µl Pfx-6 lipid (Invitrogen) for COS cells or 15 µl Pfx-7 lipid (Invitrogen) for CHO cells. Diluted DNA plus lipid was incubated with cells for 4 hr at 37° C., then replaced with the appropriate medium and incubated for an additional 40–48 hr at 37° C.

Spreading of the VP22 fusion protein from the transfected cells to the surrounding untransfected cells was detected by immunofluorescence using an antibody against the myc epitope tag. In a typical immunofluorescence experiment, transfected cells in a single 35 mm well of a six well tissue culture plate were washed with phosphate buffered saline (PBS) and fixed by incubation in 2 ml of methanol for 5 min. Cells were washed five times with PBS (2 ml/wash), blocked for 15 min using PBS containing 10% fetal bovine serum (FBS), and then incubated for 20 min with an antibody against the myc epitope tag (Invitrogen) diluted at 1:500 in 1 ml of PBS containing 10% FBS. For attachment of a fluorescent molecule to the antibody, cells were washed twice with PBS and incubated with a goat anti-mouse Oregon Green conjugate (Molecular Probes, Eugene, Oreg.; cat #O-6383) diluted 1:500 in 1 ml of PBS containing 10% FBS for 20 minutes. After two additional washes, the antigen:antibody complexes were observed using an Olympus IX-70 fluorescence microscope equipped with a fluorescein isothiocyanate (FITC) filter.

Translocation of several VP22 fusion proteins prepared in this way, including those incorporating *Aequorea victoria* green fluorescent protein (h0GFP), lacZ, or the site specific recombinase Flp as the fusion partner, has been achieved by this method.

EXAMPLE 2

Transfection of Cells with a Gene Fusion Followed by Mixing with Untransfected Cells To demonstrate how VP22 may be used to modulate expression of a functional gene product, a system for delivery of the site specific DNA recombinase Flp, was developed. COS cells expressing a VP22-Flp recombinase fusion protein were prepared as described above and mixed with CHO cells that had been transfected with a reporter plasmid pFIN4/lacZ (FIG. 1). In the reporter plasmid, a segment of DNA that includes a transcriptional terminator, the Bovine Growth Hormone polyadenylation signal (Goodwin and Rottman, *J. Biol. Chem.* 267:16330–4, 1992), is flanked by frt sites (recombination sites recognized by the recombinase Flp) to separate the CMV promoter and an otherwise operatively associated reporter gene encoding β-galactosidase as reporter. Cells transfected with pFIN4/lacZ did not express β-galactosidase due to the presence of the transcriptional terminator placed between the frt sites.

To illustrate that expression of the reporter gene could be controlled by translocating of the VP22-Flp recombinase fusion protein from one cell population to another, two populations of CHO cells were prepared, one transfected with plasmid that expresses the VP22-Flp recombinase fusion protein, and another transfected with plasmid that expresses a VP22GFP fusion protein. Transfections were carried out as described above. Twenty-four hours after the end of the transfection, cells were recovered by trypsinization. Then the two cell lines were mixed and incubated for an additional 24 hr before staining for β-galactosidase activity.

CHO cells transfected with pFIN4/lacZ only expressed β-galactosidase when mixed with COS cells that express the VP22-Flp fusion. In the presence of Flp recombinase, the segment of DNA containing the transcriptional terminator was removed by recombination of the frt sites, and β-galactosidase was expressed. Incubation of the population of CHO cells transfected with plasmid that expresses a VP22GFP fusion protein, but does not express a VP22-Flp fusion protein did not result in expression of β-galactosidase.

This experiment shows that the VP22-Flp fusion protein translocates between different mammalian cell types and that functional Flp recombinase can be delivered to cells as the fusion partner in a VP22 fusion protein.

EXAMPLE 3

Transfection of Cells with a Gene Fusion Followed by Preparation of a Cell Free Lysate from the Transfected Cells In these studies, a cell free lysate was prepared from cells transfected with pVP22/myc-His as follows: COS cells were grown to 50% confluence in a 100 mm dish (approximately $10^6$ cells). Cells were transfected with 20 μg of pVP22/myc-His DNA using Pfx-6. Forty hours post-transfection, the cell monolayer was washed twice with PBS and then collected by scraping into 10 ml PBS. Cells were centrifuged at 500 g for 5 min and the PBS was aspirated from the cell pellet, which was then frozen on dry ice. Frozen cell pellets were stored at −80° C. prior to preparation of lysates. The cell pellet was thawed on ice following addition of 0.5 ml ice cold lysis buffer (10 mM HEPES, pH 7.9, 400 mM NaCl, 0.1 mM ethylene diaminetetraacetic acid (EDTA), 0.5 mM dithiothreitol (DTT), 5% glycerol). The lysate was then vortexed briefly and centrifuged at 10000×g for 5 min at 4° C.

The entire supernatant was immediately added to $2\times10^5$ cells in a 35 mm plate without removing the tissue culture media. After a 10 minute incubation at 37° C., the media was removed and VP22/myc-His protein located in the nuclei of the cells was detected by immunofluorescence as described above.

An alternative method for the detection of VP22 fusion protein uptake in mammalian cells from a cell free lysate prepared from cells that express the fusion protein utilizes Western blot. In a typical Western blot experiment, HeLa, COS or CHO cells were plated at 50% confluence in 60 mm dishes. Following application of the lysate, the cells were washed once with PBS and then with PBS containing 500 mM NaCl to remove protein non-specifically bound to the outside of the cell. The cells were treated with trypsin for about 5 minutes to disassociate them from the plate and to digest any remaining extracellular peptide. The cells were solubilized and the proteins separated on a 4–20% Glycine gel (Invitrogen, Carlsbad, Calif.). The separated proteins were then transferred to nitrocellulose and probed with the appropriate antibody conjugated to horseradish peroxidase (HRP). The VP22 fusion proteins were then detected using chemiluminescence.

Thus, the VP22/myc-His protein contained in the lysates of cells transfected with pVP22/myc-His translocated to the nuclei of all untransfected cells within 10 minutes of contact. This finding shows that lysates containing VP22 are useful for the delivery of protein sequences into cell types without the need for transfection of the receptor cell population.

EXAMPLE 4

Expression of a VP22 Fusion Protein in E.coli. Followed by Application of Purified Protein to Cells in Culture The vector pCRT7/VP22-1 was developed to allow expression and purification of VP22 fusion proteins from E. coli. This vector utilizes a C-terminal fragment of the VP22 protein (amino acids 159–301), which has proven sufficient for translocation of VP22 fusion proteins across cell membranes. Using the above described methods, VP22 fusion proteins were prepared containing various proteins as the fusion partner (including the HIV Rev protein and human protein rhoA), and the fusion proteins were expressed and purified. Activity of each fusion partner was demonstrated following uptake by cells in culture. To demonstrate the high efficiency with which translocation occurs in cell cultures, even when the cells transfect poorly using conventional techniques, uptake of a VP22/GFP fusion proteins by Jurkat T-cells and PC12 cells, which are known to be refractory to standard transfection protocols, was also performed. These experiments show that VP22 fusion proteins can be purified and then delivered to substantially every cell in a cultured mammalian cell population, completely eliminating the need for transfection, even when the cell line is known to be refractory to standard transfection protocols.

pCRT7/VP22-1 is derived from the pET9b vector backbone (Novagen, Madison, Wis.). In preparation of pCRT7/VP22-1, the sequence encoding the C-terminal region of VP22 sufficient for translocation activity (amino acids 159–301), a fragment containing a multiple cloning site and myc and His tags from the vector pVP22/myc-His were inserted into the pET9b vector backbone. The multiple cloning site of pCRT7/VP22-1 was derived from that of pVP22/myc-His. The pCRT7/VP22-1 vector was prepared for coupling to Vaccinia Topoisomerase I in exactly the same way as in preparation of the pVP22/myc-His-TOPO® plasmid, as described above. Therefore, in this vector, the sequence encoding the ORF of a fusion partner can be either inserted into one of the multiple cloning sites or cloned as a PCR product into the topoisomerase cloning site in a way similar to that used with pVP22/myc-His or pVP22/myc-His-TOPO® plasmid.

In a typical experiment a VP22 fusion protein was expressed as follows. Ten ng pCRT7/VP22-1 DNA was transformed into 50 μl BL21(DE3)plysS cells. The transformed cells were incubated at 37° C. for 1 hour in 200 μl SOC medium, which was then diluted to 2 ml with Luria-Burtoni (LB) medium plus 50 μg/ml kanamycin and allowed to grow overnight at 37° C. The 2 ml culture was used to inoculate 50 ml LB medium containing 50 μg/ml kanamycin. Cells were allowed to grow until an optical density of 0.5–0.6 was attained and then allowed to continue growth at either 37° C., or shifted to room temperature (approximately 25° C.) for 30 min. One ml of culture was removed and allowed to continue growing. Isopropyl-β-D-thiogalactopyranoside (IPTG) was added to the remaining culture to a final concentration of 1 mM. Cells were allowed to grow for an additional 4 hours and then gel samples were prepared from induced (plus IPTG) and non-induced cultures. 200 µl of each culture were removed, cells were recovered by centrifugation, and the pellets raised in 50 µl 1×SDS/PAGE sample buffer. Alternatively, cells were recovered from the remainder of the culture by centrifugation and the cell pellets stored at −80° C.

The VP22 fusion protein was purified as follows: The cell pellet was thawed on ice and resuspended in 4 ml ice cold lysis buffer (50 mM Sodium Phosphate pH 8.0, 300 mM NaCl, 5 mM imidazole). The following were added to the lysis buffer immediately before cell lysis: β-mercaptoethanol to 5 mM, α-toluenesulfonyl fluoride (PMSF) to 0.5 mM, leupeptin and pepstatin to 1 µg/ml each, and lysozyme to 1 mg/ml. The lysate was incubated on ice for 20 to 30 min and then sonicated for 3×10 sec while on ice. DNase and RNase were added to final concentrations of 10 µg/ml each The lysate was left on ice for an additional 20 min, then drawn through a 21 gauge needle three times, and centrifuged at 20000 g for 15 min. Following centrifugation, a gel sample was prepared from the soluble supernatant. The supernatant was applied to a column containing 1 ml Probond resin equilibrated with lysis buffer (Probond beads interact with proteins tagged with 6 histidine arrays). The resin and supernatant were mixed in the column on ice for one to two hours. The column was then clamped vertically and the resin was allowed to settle.

A sample of the supernatant was removed to test for the presence of unbound protein by SDS/PAGE. The resin was washed by allowing 10 ml lysis buffer (50 mM Sodium Phosphate pH 8.0, 300 mM NaCl, 5 mM imidazole) to pass through the column. The lysis buffer was collected and a gel sample was removed. The column was then washed with 20 ml wash buffer (50 mM Sodium Phosphate pH 8.0, 300 mM NaCl, 40 mM imidazole, 10% glycerol) and another gel sample was prepared in the same way. Protein was eluted by addition of buffers having increasing concentrations of imidazole (wash buffer with either 100 mM, 200 mM or 500 mM imidazole). 3 ml of each buffer was applied, and 3 ml of each of the 100 mM and 200 mM imidazole elutions were collected. The 500 mM imidazole elution was collected as 0.5 ml fractions. A gel sample was also prepared from 10 µg of the resin after elution to determine if the protein remained bound. All samples were examined on 4–20% SDS/PAGE gels (Novex) followed by Coomassie Staining or Western blot using an anti-myc-HRP conjugated antibody (Invitrogen) at 1:2000 dilution Purified proteins were stored at 4° C. for immediate use, or frozen at −80° C. for storage.

Uptake of VP22 fusion proteins was detected by immunofluorescence. Cells were grown to approximately 50% confluence in 35 mm wells. The medium was then removed and replaced with 1 ml of serum free medium. Approximately 10 µg of the purified VP22 fusion protein, eluted in wash buffer containing 500 mM imidazole, was added directly to the serum-free medium. Cells were incubated at 37° C. for 20 min and then washed with 3×2 ml PBS. Cells were then fixed and permeablized in methanol for 5 min and prepared for immunofluorescence as described previously (see Invitrogen pVP22/myc-His Vector, cat no. V484-1).

Alternatively, uptake of VP22 fusion proteins was detected by Western blot. This technique was used to detect accumulation of VP22 fusion protein in the nuclei of PC12 cells and Jurkat T-cells. Suspensions of approximately 5×10$^5$ cells of each type were transferred to 15 ml Falcon tubes. Cells were recovered by centrifugation at 500 g for 5 min and then resuspended in 10 ml PBS. Cells were washed again in the same way, then resuspended in 1 ml serum-free medium containing approximately 10 µg of the VP22/GFP fusion protein and incubated at 37° C. for 15 min. Following the incubation, cells were washed twice by centrifugation and resuspended in 10 ml PBS as before described. Cells were recovered by centrifugation again, raised in 100 µl ice cold lysis buffer (10 mM HEPES-KOH, pH 7.9, 1.5 mM MgCl$_2$, 10 mM, KCl, 0.5 mM dithio threitol (DTT), 1% Triton X-100), and incubated on ice for 10 min. The lysate was centrifuged at 10000 g for 10 min. The supernatant, containing soluble cytoplasmic proteins, was removed, and 4×protein sample buffer was added to the supernatant. The pellet, containing cell nuclei, was resuspended in 100 µl 1×protein sample buffer. Samples were run on 4–20% SDS/PAGE gels (Novex) and transferred to nitrocellulose membrane. Western blots were probed with an anti-myc-HRP antibody conjugate (Invitrogen).

EXAMPLE 5

Activity of a VP22 Fusion Protein in Recipient Cells: Functional Testing of a VP22/Rev Fusion Protein The HIV Rev protein is encoded by HIV genomic RNA and is responsible for regulation of RNA splicing. The Rev protein can bind to transcripts that contain a Rev Response Element (RRE), allowing export of the transcript from the nucleus and subsequent translation (reviewed in V. W. Pollard et al., *Ann. Rev. Micobiol.* 52:491–532, 1998). In the absence of Rev, transcripts that contain RRE will complex with the HIV spliceosome, but are not spliced. Instead, they remain in the nucleus and are degraded.

In the following experiment, the binding of Rev to the RRE in a transcript was used to activate expression of a reporter gene. A reporter plasmid (pCAT/RRE) was prepared that contains a CMV promoter and a CAT reporter gene separated by a splice donor site. The RRE was located on the 3' side of the CAT gene site. Therefore, expression of CAT in response to Rev can be used to demonstrate the activity of Rev in the VP22/Rev fusion protein.

CHO cells were transfected with pCAT/RRE and then treated with either VP22/Rev fusion protein or VP22/myc-His control fusion protein. Expression of the CAT reporter gene was examined by Western blotting of protein samples prepared from treated cells, using an antibody against the CAT protein. A sample was also prepared from cells transfected with a CMV-CAT positive control plasmid that does not contain the RRE. Expression of the positive control could be detected. When cells were transfected with pCAT/RRE and then treated with VP22/myc-His control fusion protein, no expression of CAT could be detected. However, when cells transfected with pCAT/RRE were treated with VP22/Rev fusion protein, expression of CAT could be detected. When a five-fold larger amount of VP22/Rev protein was added, an apparent increase in the level of CAT protein was detected. These results show that VP22 can deliver functional Rev protein to the nucleus and lead to expression of a reporter gene.

In HIV infected cells, the Rev protein can shuttle between the cytoplasm and nucleus. The distribution of Rev between these intracellular compartments is dependent on a nuclear export signal present in the protein. To determine whether the nuclear export signal functioned in the invention VP22/Rev fusion protein, the distribution of VP22/Rev protein was examined by immunofluorescence using an antibody against the myc epitope tag, as described above. By this procedure, VP22/Rev fusion protein was detected in the cytoplasm and nuclei of cells, showing that fusion of Rev to VP22 appears not to interfere with the ability of Rev to be distributed to either the cytoplasm or the nucleus.

EXAMPLE 6

Delivery of One or More Molecules into Cells in Order to Modify Cellular Processes The following experiment demonstrates how a cellular process may be modified in a cell by delivery to the cell of a VP22 fusion protein that contains as the fusion partner the small GTPase, rhoA, which is involved in the polymerization of actin microfilaments in mammalian cells. Previous studies have shown that when Swiss 3T3 cells are starved of serum for 16 hr, actin microfilaments involved in maintaining the shape of cells depolymerize, leaving soluble actin monomers. Addition of serum causes rapid repolymerization of actin, restoring the microfilaments. This effect has been produced by microinjection of cells with activated rhoA protein that has been expressed and purified from E. coli (A. Hall, Science 279:509–514, 1998).

To test whether a VP22-rhoA fusion protein could generate a similar effect, a VP22-rhoA fusion protein was expressed and purified from E. coli using pCRT7/VP22-1-TOPO® plasmid. Swiss 3T3 cells were treated with the purified protein as follows: 3T3 cells were grown to approximately 50% confluence in 35 mm wells. Then the medium was removed and replaced with 1 ml of serum free medium. Cells were incubated for an additional 20 hr at 37° C. Approximately 1 µg of either purified VP22/rhoA or VP22/myc-His fusion protein was then applied to the cells. Twenty minutes later, cells were washed with 3×2 ml PBS, then fixed for 5 min in 4% formaldehyde (from Invitrogen β-galactosidase Staining Kit). Cells were washed again with 3×2 ml phosphate buffered saline (PBS), permeablized for 5 min with 0.1% Tween-20® detergent in PBS, then washed again with 2×2 ml PBS. Cells were blocked for 30 min with 10% fetal bovine serum (FBS) in PBS before incubation with 0.1 µg/ml final concentration of FITC conjugated phalloidin (Sigma P-5282) in PBS/10% FBS for 30 min.

Phalloidin binds to polymerized actin more strongly than to depolymerized actin, thus allowing for visualization of repolymerized microfilaments. Cells were washed again with 2×2 ml PBS prior to observation with an Olympus fluorescence microscope and FITC filter. The purified fusion protein was applied to serum-starved 3T3 cells. In cells that had been serum-starved and then treated with VP22/myc-His control fusion protein, no actin microfilaments could be detected and the cells appeared similar to serum-starved cells that had not been treated with either fusion protein. By contrast, in cells that had been treated with VP22-rhoA fusion protein for 20 minutes, actin microfilaments could be clearly detected by binding of phalloidin. The distribution of actin microfilaments in cells that had been treated with VP22-rhoA fusion protein appeared similar to that seen in cells that had neither been treated with a fusion protein nor serum-starved. These results indicate that VP22 can be used to deliver a functional rhoA fusion protein to cells.

The wild type rhoA protein appears to stimulate polymerization of actin microfilaments from the cell membrane, but VP22 protein is normally transported to the cell nucleus. Since VP22/rhoA could stimulate the polymerization of actin microfilaments in a similar way, the distribution of VP22/rhoA protein was examined by immunofluorescence using an antibody against the myc epitope tag of the protein (Invitrogen). Most of the VP22/rhoA fusion protein could be detected in the cytoplasm of recipient cells and very little protein appeared to reach the nuclei. These studies show that VP22/rhoA protein may be retained at the sites of rhoA activity and not completely translocated to the nucleus.

EXAMPLE 7

Delivery of a VP22 Fusion Protein to a Specific Cellular Compartment by Modification of VP22.

The following experiment demonstrates use of VP22 fusion protein to regulate distribution of the fusion partner within a specific cellular compartment. The HIV Rev protein (C. M. Troy et al., Neuroscience 16:253–61, 1996) contains a leucine rich sequence that is sufficient to direct heterologous sequences out of the nucleus and into the cytoplasm. Furthermore, it has been shown that fusion of the Nuclear Export Signal (NES) to a heterologous protein that includes the canonical SV40 larger T antigen Nuclear Localization Signal results in distribution of the protein between the cytoplasmic and nuclear compartments (W. Wen et al, Cell 82:463–473, 1995). Similarly, the Rev protein contains sequences for both nuclear import and export and is found in both the cytoplasmic and nuclear compartments (U. Fischer et al., Cell 82:475–483, 1995).

To test the ability of a translocating protein to deliver a fusion partner to a cell location other than the cell nucleus, in the present experiment, a fusion protein that consists of VP22/myc-His with the eleven amino-acid Rev NES inserted between the VP22 ORF and the myc epitope tag was expressed in E. coli, purified as described above, and applied to cells in culture.

Distribution of the fusion protein among the cellular compartments in the cells in culture was examined by immunofluorescence as described above. The distribution of the fusion protein was verified by western blot analysis of treated cells, as follows: A suspension of 5×10$^5$ cells was transferred to 15 ml Falcon tubes. Cells were recovered by centrifugation at 500 g for 5 min and then resuspended in 10 ml PBS. Cells were washed again in the same way, then resuspended in 1 ml serum-free medium containing approximately 10 µg VP22/GFP fusion protein, and incubated at 37° C. for 15 min. Following the incubation, cells were washed twice by centrifugation and resuspension in 10 ml PBS as before. Cells were recovered by centrifugation again and raised in 100 µl ice cold lysis buffer (10 mM HEPES-KOH, pH 7.9, 1.5 mM MgCl$_2$, 10 mM, KCl, 0.5 mM DTT, 1% Triton X-100® detergent) and incubated on ice for 10 min. The lysate was centrifuged at 10000 g for 10 min. The supernatant, containing soluble cytoplasmic proteins, was removed and supplemented with 4×protein sample buffer. The pellet, containing cell nuclei, was resuspended in 100 µl 1×protein sample buffer. Samples were run on 4–20% SDS/PAGE gels (Novex) and transferred to nitrocellulose membrane. Western blots were probed with an anti-myc-HRP antibody conjugate (Invitrogen). These tests show that Rev NES adapted-VP22containing fusion protein can distribute into the cytoplasm and nuclei of treated cells.

EXAMPLE 8

Use of a VP22 Fusion Protein As a Component of an Inducible Gene Expression System To test the theory that a translocating protein can be used in an inducible gene expression system with great specificity, a T7 RNAP/VP22 fusion protein was expressed and purified from *E. coli* using a protocol similar that described above for other VP22 fusion proteins. RNA polymerase activity was examined in an in vitro transcription assay. All reagents were from an in vitro transcription kit (Ambion, Austin, Tex.), and were used according to the manufacturer's instructions. The amount of RNA produced by the presence of the T7 RNAP/VP22 fusion protein was found to be similar to that of the T7 RNAP included in the kit.

A reporter construct that contains a luciferase gene driven by a T7 promoter was also constructed. This construct was transfected into COS cells and 24 hours later purified T7 RNAP/VP22 fusion protein was applied to the cells. After an additional 24 hours, cell lysates were prepared and examined for luciferase enzyme activity using a luciferase assay kit (Promega) according to the manufacturer's instructions. Addition of T7 RNAP/VP22 fusion protein to cells transfected with the reporter gene resulted in five- to ten-fold increase above background in the level of luciferase expression, indicating that this system functions to control the expression of heterologous genes in eukaryotic cells.

EXAMPLE 9

Covalent and Non-covalent Coupling to Translocating Proteins

Peptide or oligonucleotide molecules may be covalently conjugated to translocating proteins using Linx® chemical affinity system (Invitrogen) which uses low molecular weight chemical affinity ligands salicylhydroxamic acid (SHA) and phenylboronic acid (PBA). In this system, the low molecular weight chemical affinity ligands are used to form a bifunctional linker that attaches the translocating protein to a polynucleotide by means of a reversible pH-sensitive covalent bond.

Figure 3A:
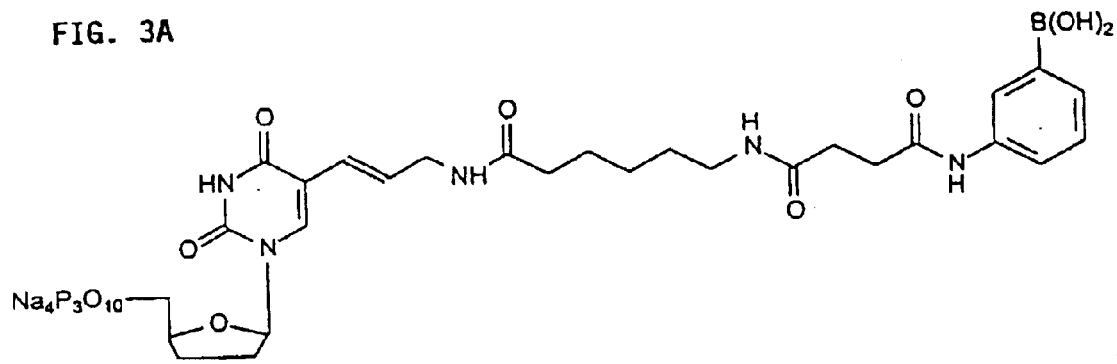
FIGS. 3A–C show the attachment of a translocating protein (VP22) to an oligonucleotide (oligo) by generation of a bifunctional linker molecule.
Figure 3B:
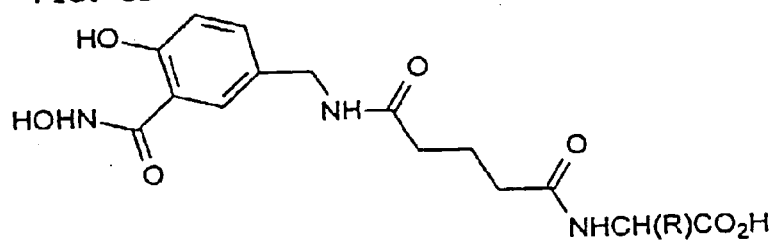
Figure 3C:
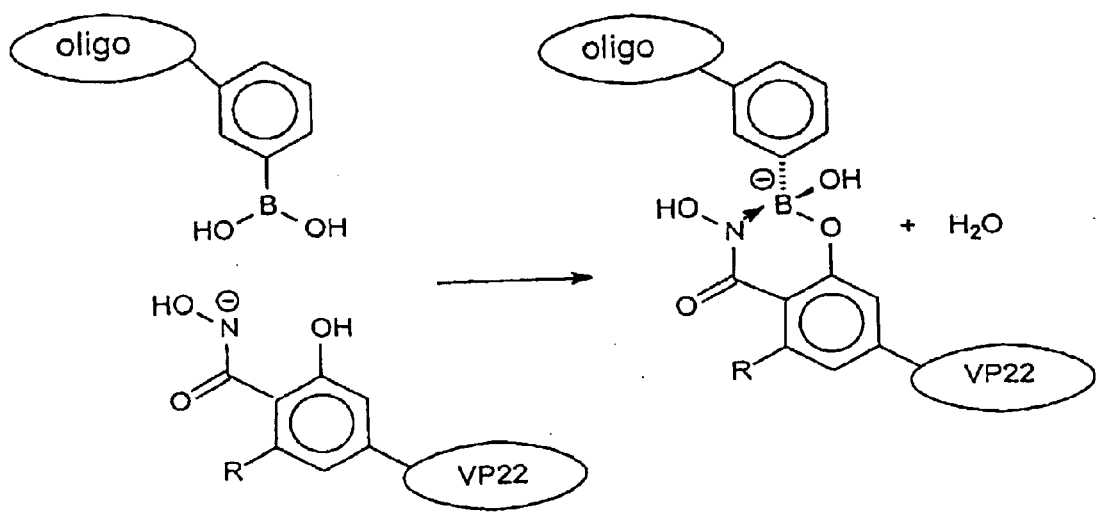

Nucleic acid molecules containing PBA can be synthesized using PBA-NTPs (ProLinx, Seattle, Wash.) or, if double stranded, labeled with PBA-ATP using the enzyme terminal transferase. SHA-NHS ester can be used to attach SHA to lysine residues present in translocating proteins (FIGS. 3A–C). The PBA-adapted molecule and the SHA-adapted translocating protein are then covalently linked and administered to cells. A full description of the procedures and conditions used to link proteins using this system is publicly available (Linx™ Rapid Protein Conjugation Kit, Catalog Nos K8050-01 to K8060-01, Invitrogen, San Diego, Calif.).

EXAMPLE 10

Assay for Uptake of Translocating Protein: Oligonucleotide Conjugates

A translocating protein and oligonucleotides of varying lengths can be conjugated and added exogenously to mammalian tissue culture cells. Single stranded DNA (ssDNA) of varying lengths containing PBA-ATP can be synthesized using PCR. A biotinylated 5' primer can be designed to allow purification of single stranded molecules containing the PBA-ATP on a strepavidin column. A series of 3' reverse primers can be generated to facilitate the synthesis of a number of ssDNA molecules between 20 and 2000 nucleotides in length. The purified ssDNA molecules containing PBA will then be mixed with the translocating protein-SHA. Different concentrations of the protein: oligonucleotide conjugate can then added to cells and allowed to incubate for up to 4 hours. After incubation, the cells can be washed, fixed, and then probed using a strepavidin-FITC conjugate. Any internalized oligonucleotides will bind the strepavidin-FITC and be detected by fluorescence. It is expected that short oligonucleotides will be internalized very efficiently (i.e. delivered to 100% of the cells) and be concentrated within the nucleus.

While the invention has been described in detail with reference to certain preferred embodiments thereof, it will be understood that modifications and variations are within the spirit and scope of that which is described and claimed.

What is claimed is:

1. A method for modulating expression of a target gene product in a cell in culture that contains a target gene under control of one or more regulatory elements, said method comprising contacting the cell in culture under suitable conditions with one or more regulatory agents attached to a translocating polypeptide, whereby the one or more regulatory agents are translocated into the cell in culture and interact therein with the one or more regulatory elements, thereby modulating expression of the target gene product by the cell wherein the translocating polypeptide exhibits receptor-independent and energy-free penetration of cell membranes, wherein the cell does not have a cell wall; and wherein the one or more regulatory agents include a recombinase.

2. The method according to claim 2 wherein the cell in culture is a mammalian, or insect cell.

3. The method according to claim 1 wherein the translocating polypeptide is a VP22 polypeptide, Antp, or Protein H.

4. The method according to claim 1 wherein the translocating polypeptide is a VP22 polypeptide.

5. A method for modulating expression of a target gene product in a cell in culture that contains a target gene under control of one or more regulatory elements, said method comprising contacting the cell under suitable conditions with one or more regulatory agents attached to a translocating polypeptide, whereby the one or more regulatory agents are translocated into the cell in culture and interact therein with the one or more regulatory elements, thereby modulating expression of the target gene product by the cell wherein the translocating polypeptide exhibits receptor-independent and energy-free penetration of cell membranes, wherein the cell does not have a cell wall; wherein the one or more regulatory elements includes a promoter and wherein the one or more regulatory agents include a polymerase specific for the promoter.

6. The method according to claim 5 wherein the polymerase is T7 RNA polymerase and the promoter is a T7 promoter.

7. A method for modulating expression of a target gene product in a cell in culture that contains a target gene under control of one or more regulatory elements, said method comprising contacting the cell under suitable conditions with one or more regulatory agents attached to a translocating polypeptide, whereby the one or more regulatory agents are translocated into the cell in culture and interact therein with the one or more regulatory elements, thereby modulating expression of the target gene product by the cell wherein the translocating polypeptide exhibits receptor-independent and energy-free penetration of cell membranes, wherein the cell does not have a cell wall; wherein the one or more regulatory agents include an HIV Rev protein and the one or more regulatory elements include the HIV Rev response element (RRE).

8. The method according to claim 1 wherein the one or more regulatory agents and the translocating polypeptide are covalently attached.

9. The method according to claim 1 wherein the one or more regulatory agents and the translocating polypeptide are attached by a linker.

10. The method according to claim 9 wherein the linker comprises one or more disulfide bonds, salicylhydroxamic acid (SHA), phenylboronic acid (PBA), a SHA-NHS ester, or a combination thereof.

11. The method according to claim 1 wherein the translocating polypeptide and the one or more regulatory agents are units of a fusion protein.

12. The method according to claim 1 wherein the translocating polypeptide and the one or more regulatory agents are linked by a biotin-streptavidin complex or the E. Coli single stranded DNA binding protein.

13. The method according to claim 1 wherein the one or more regulatory agents include a site-specific recombinase, the cell contains a first nucleic acid with at least one site-specific genomic recombination site, and a second nucleic acid containing the target gene and at least one site-specific recombination site wherein the recombinase is specific for the recombination sites, and wherein translocation of the site-specific recombinase causes recombination between the site-specific recombination sites resulting in stable integration of the target gene into the genome of the cell at the genomic recombination site.

14. The method according to claim 13 wherein the recombinase is a member of a family of site-specific recombinases selected from the groups consisting of the integrase family of site-specific recombinases and the resolvase/invertase family of site-specific recombinases.

15. The method according to claim 13 wherein the site-specific recombination sites are frt sites and the site-specific recombinase is Flp or the site-specific recombination sites are lox recombination sites and the site-specific recombinase is Cre.

16. The method according to claim 1 wherein the one or more regulatory agents include a site-specific recombinase which excises, the one or more regulatory elements of the target gene, thereby modulating expression of the target gene product.

17. The method according to claim 16 wherein the site-specific recombinase is Flp or Cre.

18. The method according to claim 1 wherein the target gene is a reporter gene.

19. The method according to claim 1 wherein the target gene is contained within a polynucleotide that further encodes a protein tag.

20. The method according to claim 1 wherein the target gene encodes a toxic protein.

21. The method according to claim 19 wherein the protein tag is a myc epitope, a fluorescent peptide, or a poly His tag, or a combination of any two or more thereof.

22. The method of claim 1 wherein the cell in culture is a eukaryotic cell.

23. The method according to claim 1 wherein the one or more regulatory agents and the translocating polypeptide are non-covalently attached.

24. The method according to claim 1 wherein the recombinase is a site-specific recombinase and a nucleic acid comprising the target gene further comprises one or more site-specific recombination sites.

25. The method of claim 24 wherein the site-specific recombinase is a member of a family of site-specific recombinases selected from the group consisting of the integrase family of site-specific recombinases and the resolvase/invertase family of site-specific recombinases.

26. The method according to claim 25 wherein the site-specific recombination sites are frt sites and the site-specific recombinase is Flp or the site-specific recombination sites are lox recombination sites and the site-specific recombinase is Cre.

27. A method for modulating expression of a target gene product in a cell in culture that contains a target gene under control of one or more regulatory elements, said method comprising contacting the cell under suitable conditions with one or more regulatory agents attached to a translocating polypeptide, whereby the one or more regulatory agents are translocated into the cell in culture and interact therein with the one or more regulatory elements, thereby modulating expression of the target gene product by the cell wherein the translocating polypeptide exhibits receptor-independent and energy-free penetration of cell membranes, wherein the cell does not have a cell wall; and wherein the one or more regulatory agents include a DNA-binding protein wherein the DNA-binding domain is that of SEQ ID No: 4.

28. A method for modulating expression of a target gene product in a cell in culture that contains a target gene under control of one or more regulatory elements, said method comprising contacting the cell under suitable conditions with one or more regulatory agents attached to a translocating polypeptide, whereby the one or more regulatory agents are translocated into the cell in culture and interact therein with the one or more regulatory elements, thereby modulating expression of the target gene product by the cell wherein the translocating polypeptide exhibits receptor-independent and energy-free penetration of cell membranes, wherein the cell does not have a cell wall; and wherein the one or more regulatory agents include a DNA-binding protein wherein the DNA-binding protein is a histone 1(H1) protein or a non-histone protein HMG-17.

29. The method according to claim 1 wherein the translocating polypeptide and the one or more regulatory agents are linked by a Vaccinia topoisomerase I linker.

30. The method according to claim 5 wherein the translocating polypeptide is a VP22 polypeptide.

31. The method according to claim 7 herein the translocating polypeptide is a VP22 polypeptide.

32. The method according to claim 27 wherein the translocating polypeptide is a VP22 polypeptide.

33. The method according to claim 5 wherein the translocating polypeptide and the one or more regulatory agents are units of a fusion protein.

34. The method according to claim 7 wherein the translocating polypeptide and the one or more regulatory agents are units of a fusion protein.

35. The method according to claim 27 wherein the translocating polypeptide and the one or more regulatory agents are units of a fusion protein.

36. The method according to claim 28 wherein the translocating polypeptide is a VP22 polypeptide.

37. The method according to claim 28 wherein the translocating polypeptide and the one or more regulatory agents are units of a fusion protein.

* * * * *

SEQUENCE LISTING

```
<160> NUMBER OF SEQ ID NOS: 21

<210> SEQ ID NO 1
<211> LENGTH: 6404
<212> TYPE: DNA
<213> ORGANISM: Artificial Sequence
<220> FEATURE:
<223> OTHER INFORMATION: vector pVP22/Myc-His

<400> SEQUENCE: 1
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
```

-continued

```
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg       780
gtaggcgtgt acggtgggag gtctatataa gcagagctct ctggctaact agagaaccca      840
ctgcttactg gcttatcgaa attaatacga ctcactatag ggagacccaa gctggctagt      900
taagcttatt atgacctctc gccgctccgt gaagtcgggt ccgcgggagg ttccgcgcga      960
tgagtacgag gatctgtact acaccccgtc ttcaggtatg gcgagtcccg atagtccgcc     1020
tgacacctcc cgccgtggcg ccctacagac acgctcgcgc cagaggggcg aggtccgttt     1080
cgtccagtac gacgagtcgg attatgccct ctacggggc tcgtcttccg aagacgacga      1140 acaccggag gtcccccgga cgcggcgtcc cgtttccggg gcggttttgt ccggcccggg      1200
gcctgcgcgg gcgcctccgc cacccgctgg gtccggaggg gccggacgca cacccaccac     1260
cgccccccgg gcccccgaa cccagcgggt ggcgtctaag gcccccgcgg ccccggcggc      1320
ggagaccacc cgcggcagga aatcggccca gccagaatcc gccgcactcc cagacgcccc     1380
cgcgtcgacg gcgccaaccc gatccaagac acccgcgcag gggctggcca gaaagctgca     1440 cttttagcacc gcccccccaa accccgacgg gccatggacc ccccgggtgg ccggctttaa    1500
caagcgcgtc ttctgcgccg cggtcgggcg cctggcggcc atgcatgccc ggatggcggc     1560
tgtccagctc tgggacatgt cgcgtccgcg cacagacgaa gacctcaacg aactccttgg     1620
catcaccacc atccgcgtga cggtctgcga gggcaaaaac ctgcttcagc gcgccaacga     1680
gttggtgaat ccagacgtgg tgcaggacgt cgacgcggcc acggcgactc gagggcgttc     1740
tgcggcgtcg cgccccaccg agcgacctcg agccccagcc cgctccgctt ctcgccccag     1800
acggcccgtc gagggtaccg agctcggatc cactagtcca gtgtggtgga attctgcaga     1860
tatccagcac agtggcggcc gctcgagtct agagggcccg cggttcgaac aaaaactcat     1920
ctcagaagag gatctgaata tgcataccgg tcatcatcac catcaccatt gagtttaaac     1980
ccgctgatca gcctcgactg tgccttctag ttgccagcca tctgttgttt gcccctcccc     2040
cgtgccttcc ttgaccctgg aaggtgccac tcccactgtc ctttcctaat aaaatgagga     2100
aattgcatcg cattgtctga gtaggtgtca ttctattctg ggggggtgggg tggggcagga   2160 cagcaagggg gaggattggg aagacaatag caggcatgct ggggatgcgg tgggctctat     2220
ggcttctgag gcgaaagaa ccagctgggg ctctaggggg tatccccacg cgccctgtag      2280
cggcgcatta agcgcggcgg gtgtggtggt tacgcgcagc gtgaccgcta cacttgccag     2340
cgccctagcg cccgctcctt tcgctttctt cccttccttt ctcgccacgt tcgccggctt     2400
tccccgtcaa gctctaaatc gggcatccc tttagggttc cgatttagtg ctttacggca     2460
cctcgacccc aaaaaacttg attagggtga tggttcacgt agtgggccat cgccctgata     2520
gacggttttt cgccctttga cgttggagtc acgttctttt aatagtggac tcttgttcca    2580
aactggaaca acactcaacc ctatctcggt ctattctttt gatttataag ggattttggg     2640
gatttcggcc tattggttaa aaaatgagct gatttaacaa aaatttaacg cgaattaatt     2700
ctgtggaatg tgtgtcagtt agggtgtgga aagtccccag gctccccagg caggcagaag     2760
tatgcaaagc atgcatctca attagtcagc aaccaggtgt ggaaagtccc caggctcccc    2820
```

-continued

```
agcaggcaga agtatgcaaa gcatgcatct caattagtca gcaaccatag tcccgcccct    2880
aactccgccc atcccgcccc taactccgcc cagttccgcc cattctccgc cccatggctg    2940
actaattttt tttatttatg cagaggccga ggccgcctct gcctctgagc tattccagaa    3000
gtagtgagga ggcttttttg gaggcctagg cttttgcaaa aagctcccgg gagcttgtat    3060
atccattttc ggatctgatc aagagacagg atgaggatcg tttcgcatga ttgaacaaga    3120
tggattgcac gcaggttctc cggccgcttg ggtggagagg ctattcggct atgactgggc    3180
acaacagaca atcggctgct ctgatgccgc cgtgttccgg ctgtcagcgc aggggcgccc    3240
ggttctttt gtcaagaccg acctgtccgg tgccctgaat gaactgcagg acgaggcagc    3300
gcggctatcg tggctggcca cgacgggcgt tccttgcgca gctgtgctcg acgttgtcac    3360
tgaagcggga agggactggc tgctattggg cgaagtgccg gggcaggatc tcctgtcatc    3420
tcaccttgct cctgccgaga aagtatccat catggctgat gcaatgcggc ggctgcatac    3480
gcttgatccg gctacctgcc cattcgacca ccaagcgaaa catcgcatcg agcgagcacg    3540
tactcggatg aagccggtc ttgtcgatca ggatgatctg gacgaagagc atcaggggct    3600
cgcgccagcc gaactgttcg ccaggctcaa ggcgcgcatg cccgacggcg aggatctcgt    3660
cgtgacccat ggcgatgcct gcttgccgaa tatcatggtg aaaatggcc gcttttctgg    3720
attcatcgac tgtggccggc tgggtgtggc ggaccgctat caggacatag cgttggctac    3780
ccgtgatatt gctgaagagc ttggcggcga atgggctgac cgcttcctcg tgctttacgg    3840
tatcgccgct cccgattcgc agcgcatcgc cttctatcgc cttcttgacg agttcttctg    3900
agcgggactc tggggttcgc gaaatgaccg accaagcgac gcccaacctg ccatcacgag    3960
atttcgattc caccgccgcc ttctatgaaa ggttgggctt cggaatcgtt ttccgggacg    4020
ccggctggat gatcctccag cgcggggatc tcatgctgga gttcttcgcc caccccaact    4080
tgtttattgc agcttataat ggttacaaat aaagcaatag catcacaaat ttcacaaata    4140
aagcattttt ttcactgcat tctagttgtg gtttgtccaa actcatcaat gtatcttatc    4200
atgtctgtat accgtcgacc tctagctaga gcttggcgta atcatggtca tagctgtttc    4260
ctgtgtgaaa ttgttatccg ctcacaattc cacacaacat acgagccgga agcataaagt    4320
gtaaagcctg gggtgcctaa tgagtgagct aactcacatt aattgcgttg cgctcactgc    4380
ccgctttcca gtcgggaaac ctgtcgtgcc agctgcatta atgaatcggc caacgcgcgg    4440
ggagaggcgg tttgcgtatt gggcgctctt ccgcttcctc gctcactgac tcgctgcgct    4500
cggtcgttcg gctgcggcga gcggtatcag ctcactcaaa ggcggtaata cggttatcca    4560
cagaatcagg ggataacgca ggaaagaaca tgtgagcaaa aggccagcaa aaggccagga    4620
accgtaaaaa ggccgcgttg ctggcgtttt tccataggct ccgcccccct gacgagcatc    4680
acaaaaatcg acgctcaagt cagaggtggc gaaacccgac aggactataa agataccagg    4740
cgtttccccc tggaagctcc ctcgtgcgct ctcctgttcc gaccctgccg cttaccggat    4800
acctgtccgc ctttctccct tcgggaagcg tggcgctttc tcaatgctca cgctgtaggt    4860
atctcagttc ggtgtaggtc gttcgctcca agctgggctg tgtgcacgaa ccccccgttc    4920
agcccgaccg ctgcgcctta tccggtaact atcgtcttga gtccaacccg gtaagacacg    4980
acttatcgcc actggcagca gccactggta acaggattag cagagcgagg tatgtaggcg    5040
gtgctacaga gttcttgaag tggtggccta actacggcta cactagaagg acagtatttg    5100
gtatctgcgc tctgctgaag ccagttacct tcggaaaaag agttggtagc tcttgatccg    5160
gcaaacaaac caccgctggt agcggtggtt ttttgtttg caagcagcag attacgcgca    5220
```

-continued

```
gaaaaaaagg atctcaagaa gatcctttga tcttttctac ggggtctgac gctcagtgga    5280
acgaaaactc acgttaaggg attttggtca tgagattatc aaaaaggatc ttcacctaga    5340
tccttttaaa ttaaaaatga agttttaaat caatctaaag tatatatgag taaacttggt    5400
ctgacagtta ccaatgctta atcagtgagg cacctatctc agcgatctgt ctatttcgtt    5460
catccatagt tgcctgactc cccgtcgtgt agataactac gatacgggag ggcttaccat    5520
ctggccccag tgctgcaatg ataccgcgag acccacgctc accggctcca gatttatcag    5580
caataaacca gccagccgga agggccgagc gcagaagtgg tcctgcaact ttatccgcct    5640
ccatccagtc tattaattgt tgccgggaag ctagagtaag tagttcgcca gttaatagtt    5700
tgcgcaacgt tgttgccatt gctacaggca tcgtggtgtc acgctcgtcg tttggtatgg    5760
cttcattcag ctccggttcc caacgatcaa ggcgagttac atgatccccc atgttgtgca    5820
aaaaagcggt tagctccttc ggtcctccga tcgttgtcag aagtaagttg gccgcagtgt    5880
tatcactcat ggttatggca gcactgcata attctcttac tgtcatgcca tccgtaagat    5940
gcttttctgt gactggtgag tactcaacca agtcattctg agaatagtgt atgcggcgac    6000
cgagttgctc ttgcccggcg tcaatacggg ataataccgc gccacatagc agaactttaa    6060
aagtgctcat cattggaaaa cgttcttcgg ggcgaaaact ctcaaggatc ttaccgctgt    6120
tgagatccag ttcgatgtaa cccactcgtg cacccaactg atcttcagca tcttttactt    6180
tcaccagcgt ttctgggtga gcaaaaacag gaaggcaaaa tgccgcaaaa aagggaataa    6240
gggcgacacg gaaatgttga atactcatac tcttcctttt tcaatattat tgaagcattt    6300
atcagggtta ttgtctcatg agcggataca tatttgaatg tatttagaaa aataaacaaa    6360 tagggggttcc gcgcacattt ccccgaaaag tgccacctga cgtc                    6404
```

<210> SEQ ID NO 2
<211> LENGTH: 6420
<212> TYPE: DNA
<213> ORGANISM: Artificial Sequence
<220> FEATURE:
<223> OTHER INFORMATION: vector pVP22/Myc-His-TOPO

<400> SEQUENCE: 2

```
gacggatcgg gagatctccc gatccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgcc ccattgacg caaatgggcg    780 gtaggcgtgt acggtgggag gtctatataa gcagagctct ctggctaact agagaaccca    840
```

| | |
|---|---|
| ctgcttactg gcttatcgaa attaatacga ctcactatag ggagacccaa gctggctagt | 900 |
| taagcttatt atgacctctc gccgctccgt gaagtcgggt ccgcgggagg ttccgcgcga | 960 |
| tgagtacgag gatctgtact acaccccgtc ttcaggtatg gcgagtcccg atagtccgcc | 1020 |
| tgacacctcc cgccgtggcg ccctacagac acgctcgcgc cagaggggcg aggtccgttt | 1080 |
| cgtccagtac gacgagtcgg attatgccct ctacggggc tcgtcttccg aagacgacga | 1140 |
| acaccccggag gtcccccgga cgcggcgtcc cgtttccggg gcggttttgt ccggcccggg | 1200 |
| gcctgcgcgg gcgcctccgc cacccgctgg gtccggaggg gccggacgca cacccaccac | 1260 |
| cgcccccgg gcccccgaa cccagcgggt ggcgactaag gccccgcgg ccccggcggc | 1320 |
| ggagaccacc cgcggcagga aatcggccca gccagaatcc gccgcactcc cagacgcccc | 1380 |
| cgcgtcgacg gcgccaaccc gatccaagac acccgcgcag gggctggcca gaaagctgca | 1440 |
| ctttagcacc gccccccaa accccgacgc gccatggacc ccccgggtgg ccggctttaa | 1500 |
| caagcgcgtc ttctgcgccg cggtcggcgc cctggcggcc atgcatgccc ggatggcggc | 1560 |
| ggtccagctc tgggacatgt cgcgtccgcg cacagacgaa gacctcaacg aactccttgg | 1620 |
| catcaccacc atccgcgtga cggtctgcga gggcaaaaac ctgcttcagc gcgccaacga | 1680 |
| gttggtgaat ccagacgtgg tgcaggacgt cgacgcggcc acggcgactc gagggcgttc | 1740 |
| tgcggcgtcg cgccccaccg agcgacctcg agccccagcc cgctccgctt ctcgccccag | 1800 |
| acggcccgtc gagggtaccg agctcggatc cactagtcca gtgtggtgga attgcccttta | 1860 |
| agggcaattc tgcagatatc cagcacagtg gcggccgctc gagtctagag ggcccgcggt | 1920 |
| tcgaacaaaa actcatctca gaagaggatc tgaatatgca taccggtcat catcaccatc | 1980 |
| accattgagt ttaaacccgc tgatcagcct cgactgtgcc ttctagttgc cagccatctg | 2040 |
| ttgtttgccc ctcccccgtg ccttccttga ccctggaagg tgccactccc actgtccttt | 2100 |
| cctaataaaa tgaggaaatt gcatcgcatt gtctgagtag gtgtcattct attctggggg | 2160 |
| gtggggtggg gcaggacagc aagggggagg attgggaaga caatagcagg catgctgggg | 2220 |
| atgcggtggg ctctatggct tctgaggcgg aaagaaccag ctggggctct agggggtatc | 2280 |
| cccacgcgcc ctgtagcggc gcattaagcg cggcgggtgt ggtggttacg cgcagcgtga | 2340 |
| ccgctacact tgccagcgcc ctagcgcccg ctcctttcgc tttcttccct tcctttctcg | 2400 |
| ccacgttcgc cggctttccc cgtcaagctc taaatcgggg catccctta gggttccgat | 2460 |
| ttagtgcttt acggcacctc gaccccaaaa aacttgatta gggtgatggt tcacgtagtg | 2520 |
| ggccatcgcc ctgatagacg gttttcgcc ctttgacgtt ggagtccacg ttctttaata | 2580 |
| gtggactctt gttccaaact ggaacaacac tcaaccctat ctcggtctat tcttttgatt | 2640 |
| tataaggat tttgggatt tcggcctatt ggttaaaaaa tgagctgatt taacaaaaat | 2700 |
| ttaacgcgaa ttaattctgt ggaatgtgtg tcagttaggg tgtggaaagt ccccaggctc | 2760 |
| cccaggcagg cagaagtatg caaagcatgc atctcaatta gtcagcaacc aggtgtggaa | 2820 |
| agtccccagg ctccccagca ggcagaagta tgcaaagcat gcatctcaat tagtcagcaa | 2880 |
| ccatagtccc gccctaact ccgcccatcc cgcccctaac tccgcccagt tccgcccatt | 2940 |
| ctccgcccca tggctgacta attttttta tttatgcaga ggccgaggcc gcctctgcct | 3000 |
| ctgagctatt ccagaagtag tgaggaggct ttttggagg cctaggcttt tgcaaaaagc | 3060 |
| tcccgggagc ttgtatatcc attttcggat ctgatcaaga acaggatga ggatcgtttc | 3120 |
| gcatgattga acaagatgga ttgcacgcag gttctccggc cgcttgggtg gagaggctat | 3180 |
| tcggctatga ctgggcacaa cagacaatcg gctgctctga tgccgccgtg ttccggctgt | 3240 |

```
cagcgcaggg gcgcccggtt cttttgtca agaccgacct gtccggtgcc ctgaatgaac   3300
tgcaggacga ggcagcgcgg ctatcgtggc tggccacgac gggcgttcct tgcgcagctg   3360
tgctcgacgt tgtcactgaa gcgggaaggg actggctgct attgggcgaa gtgccggggc   3420
aggatctcct gtcatctcac cttgctcctg ccgagaaagt atccatcatg gctgatgcaa   3480
tgcggcggct gcatacgctt gatccggcta cctgcccatt cgaccaccaa gcgaaacatc   3540
gcatcgagcg agcacgtact cggatggaag ccggtcttgt cgatcaggat gatctggacg   3600
aagagcatca gggctcgcg ccagccgaac tgttcgccag gctcaaggcg cgcatgcccg   3660
acggcgagga tctcgtcgtg acccatggcg atgcctgctt gccgaatatc atggtggaaa   3720
atggccgctt ttctggattc atcgactgtg gccggctggg tgtggcggac cgctatcagg   3780
acatagcgtt ggctacccgt gatattgctg aagagcttgg cggcgaatgg gctgaccgct   3840
tcctcgtgct ttacggtatc gccgctcccg attcgcagcg catcgccttc tatcgccttc   3900
ttgacgagtt cttctgagcg ggactctggg gttcgcgaaa tgaccgacca agcgacgccc   3960
aacctgccat cacgagattt cgattccacc gccgccttct atgaaaggtt gggcttcgga   4020
atcgttttcc gggacgccgg ctggatgatc ctccagcgcg gggatctcat gctggagttc   4080
ttcgcccacc ccaacttgtt tattgcagct tataatggtt acaaataaag caatagcatc   4140
acaaatttca caaataaagc attttttca ctgcattcta gttgtggttt gtccaaactc   4200
atcaatgtat cttatcatgt ctgtataccg tcgacctcta gctagagctt ggcgtaatca   4260
tggtcatagc tgtttcctgt gtgaaattgt tatccgctca caattccaca acatacga   4320
gccggaagca taaagtgtaa agcctggggt gcctaatgag tgagctaact cacattaatt   4380
gcgttgcgct cactgcccgc tttccagtcg ggaaacctgt cgtgccagct gcattaatga   4440
atcggccaac gcgcggggag aggcggtttg cgtattgggc gctcttccgc ttcctcgctc   4500
actgactcgc tgcgctcggt cgttcggctg cggcgagcgg tatcagctca ctcaaaggcg   4560
gtaatacggt tatccacaga atcagggga t aacgcaggaa agaacatgtg agcaaaaggc   4620
cagcaaaagg ccaggaaccg taaaaaggcc gcgttgctgg cgtttttcca taggctccgc   4680
cccctgacg agcatcacaa aaatcgacgc tcaagtcaga ggtggcgaaa cccgacagga   4740
ctataaagat accaggcgtt tccccctgga agctccctcg tgcgctctcc tgttccgacc   4800
ctgccgctta ccggatacct gtccgccttt ctcccttcgg gaagcgtggc gctttctcaa   4860
tgctcacgct gtaggtatct cagttcggtg taggtcgttc gctccaagct gggctgtgtg   4920
cacgaacccc ccgttcagcc cgaccgctgc gccttatccg gtaactatcg tcttgagtcc   4980
aacccggtaa gacacgactt atcgccactg gcagcagcca ctggtaacag gattagcaga   5040
gcgaggtatg taggcggtgc tacagagttc ttgaagtggt ggcctaacta cggctacact   5100
agaaggacag tatttggtat ctgcgctctg ctgaagccag ttaccttcgg aaaaagagtt   5160
ggtagctctt gatccggcaa acaaaccacc gctggtagcg gtggtttttt tgtttgcaag   5220
cagcagatta cgcgcagaaa aaaggatct caagaagatc ctttgatctt ttctacgggg   5280
tctgacgctc agtggaacga aaactcacgt taagggattt tggtcatgag attatcaaaa   5340
aggatcttca cctagatcct tttaaattaa aatgaagtt ttaaatcaat ctaaagtata   5400
tatgagtaaa cttggtctga cagttaccaa tgcttaatca gtgaggcacc tatctcagcg   5460
atctgtctat ttcgttcatc catagttgcc tgactcccccg tcgtgtagat aactacgata   5520
cgggagggct taccatctgg ccccagtgct gcaatgatac cgcgagaccc acgctcaccg   5580
```

```
gctccagatt tatcagcaat aaaccagcca gccggaaggg ccgagcgcag aagtggtcct   5640
gcaactttat ccgcctccat ccagtctatt aattgttgcc gggaagctag agtaagtagt   5700
tcgccagtta atagtttgcg caacgttgtt gccattgcta caggcatcgt ggtgtcacgc   5760
tcgtcgtttg gtatggcttc attcagctcc ggttcccaac gatcaaggcg agttacatga   5820
tcccccatgt tgtgcaaaaa agcggttagc tccttcggtc ctccgatcgt tgtcagaagt   5880
aagttggccg cagtgttatc actcatggtt atggcagcac tgcataattc tcttactgtc   5940
atgccatccg taagatgctt ttctgtgact ggtgagtact caaccaagtc attctgagaa   6000
tagtgtatgc ggcgaccgag ttgctcttgc ccggcgtcaa tacgggataa taccgcgcca   6060
catagcagaa ctttaaaagt gctcatcatt ggaaaacgtt cttcggggcg aaaactctca   6120
aggatcttac cgctgttgag atccagttcg atgtaaccca ctcgtgcacc caactgatct   6180
tcagcatctt ttactttcac cagcgtttct gggtgagcaa aaacaggaag gcaaaatgcc   6240
gcaaaaaagg gaataagggc gacacggaaa tgttgaatac tcatactctt cctttttcaa   6300
tattattgaa gcatttatca gggttattgt ctcatgagcg gatacatatt tgaatgtatt   6360
tagaaaaata aacaaatagg ggttccgcgc acatttcccc gaaaagtgcc acctgacgtc   6420
```

<210> SEQ ID NO 3
<211> LENGTH: 12
<212> TYPE: PRT
<213> ORGANISM: Artificial Sequence
<220> FEATURE:
<223> OTHER INFORMATION: Peptide linker

<400> SEQUENCE: 3

Leu Ala Arg Leu Leu Ala Arg Leu Leu Ala Arg Leu
 1               5                  10

<210> SEQ ID NO 4
<211> LENGTH: 67
<212> TYPE: PRT
<213> ORGANISM: Artificial sequence
<220> FEATURE:
<223> OTHER INFORMATION: Conserved sequence of steroid/thyroid hormone
      receptor superfamily DNA-binding domain
<221> NAME/KEY: VARIANT
<222> LOCATION: (0)...(0)
<223> OTHER INFORMATION: Xaa is non-conserved amino acids within the
      DNA-binding domain
<221> NAME/KEY: VARIANT
<222> LOCATION: 7, 9, 11, 13, 22, 27, 58, 61, 66
<223> OTHER INFORMATION: amino acid residues that are almost universally
      conserved, but for which variations have been
      found in some identified hormone receptors

<400> SEQUENCE: 4

Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa Xaa
                20                  25                  30

Xaa Xaa Cys Xaa Xaa Xaa Xaa Xaa Xaa Xaa Cys Xaa Xaa Xaa Lys
        35                  40                  45

Xaa Xaa Arg Xaa Xaa Cys Xaa Xaa Cys Arg Xaa Xaa Lys Cys Xaa Xaa
    50                  55                  60

Xaa Gly Met
65

<210> SEQ ID NO 5
<211> LENGTH: 34

```
<212> TYPE: DNA
<213> ORGANISM: Bacteriophage P1

<400> SEQUENCE: 5
ataacttcgt atagcataca ttatacgaag ttat                            34

<210> SEQ ID NO 6
<211> LENGTH: 34
<212> TYPE: DNA
<213> ORGANISM: E. coli

<400> SEQUENCE: 6
ataacttcgt atagtataca ttatacgaag ttat                            34

<210> SEQ ID NO 7
<211> LENGTH: 34
<212> TYPE: DNA
<213> ORGANISM: E. coli

<400> SEQUENCE: 7
acaacttcgt ataatgtatg ctatacgaag ttat                            34

<210> SEQ ID NO 8
<211> LENGTH: 34
<212> TYPE: DNA
<213> ORGANISM: Saccharomyces cerevisiae

<400> SEQUENCE: 8
gaagttccta ttctctagaa agtataggaa cttc                            34

<210> SEQ ID NO 9
<211> LENGTH: 5
<212> TYPE: PRT
<213> ORGANISM: Artificial Sequence
<220> FEATURE:
<223> OTHER INFORMATION: peptide linker moiety

<400> SEQUENCE: 9

Gly Gly Gly Gly Ser
 1               5

<210> SEQ ID NO 10
<211> LENGTH: 5
<212> TYPE: PRT
<213> ORGANISM: Artificial Sequence
<220> FEATURE:
<223> OTHER INFORMATION: Peptide linker moiety; sequence can be repeated
      indefinit number of times

<400> SEQUENCE: 10

Gly Gly Gly Gly Ser
 1               5

<210> SEQ ID NO 11
<211> LENGTH: 12
<212> TYPE: PRT
<213> ORGANISM: Artificial Sequence
<220> FEATURE:
<223> OTHER INFORMATION: Peptide linker moiety

<400> SEQUENCE: 11

Gly Lys Ser Ser Gly Ser Gly Ser Glu Ser Lys Ser
 1               5                  10

<210> SEQ ID NO 12
```

-continued

```
<211> LENGTH: 14
<212> TYPE: PRT
<213> ORGANISM: Artificial Sequence
<220> FEATURE:
<223> OTHER INFORMATION: Peptide linker moiety

<400> SEQUENCE: 12

Gly Ser Thr Ser Gly Ser Gly Lys Ser Ser Glu Gly Lys Gly
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Peptide linker moiety

<400> SEQUENCE: 13

Gly Ser Thr Ser Gly Ser Gly Lys Ser Ser Glu Gly Ser Gly Ser Thr
1               5                   10                  15

Lys Gly

<210> SEQ ID NO 14
<211> LENGTH: 14
<212> TYPE: PRT
<213> ORGANISM: Artificial Sequence
<220> FEATURE:
<223> OTHER INFORMATION: Peptide linker moiety

<400> SEQUENCE: 14

Gly Ser Thr Ser Gly Ser Gly Lys Ser Ser Glu Gly Lys Gly
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Peptide linker moiety

<400> SEQUENCE: 15

Gly Ser Thr Ser Gly Ser Gly Lys Pro Gly Ser Gly Glu Gly Ser Thr
1               5                   10                  15

Lys Gly

<210> SEQ ID NO 16
<211> LENGTH: 14
<212> TYPE: PRT
<213> ORGANISM: Artificial Sequence
<220> FEATURE:
<223> OTHER INFORMATION: Peptide linker moiety

<400> SEQUENCE: 16

Glu Gly Lys Ser Ser Gly Ser Gly Ser Glu Ser Lys Glu Phe
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Peptide linker moiety

<400> SEQUENCE: 17

Ser Arg Ser Ser Gly
1               5
```

-continued

```
<210> SEQ ID NO 18
<211> LENGTH: 5
<212> TYPE: PRT
<213> ORGANISM: Artificial Sequence
<220> FEATURE:
<223> OTHER INFORMATION: Peptide linker moiety

<400> SEQUENCE: 18

Ser Gly Ser Ser Cys
 1               5

<210> SEQ ID NO 19
<211> LENGTH: 27
<212> TYPE: PRT
<213> ORGANISM: Artificial Sequence
<220> FEATURE:
<223> OTHER INFORMATION: Peptide linker moiety

<400> SEQUENCE: 19

Met Gly Arg Ser Gly Gly Gly Cys Ala Gly Asn Arg Val Gly Ser Ser
 1               5                  10                  15

Leu Ser Cys Gly Gly Leu Asn Leu Gln Ala Met
            20                  25

<210> SEQ ID NO 20
<211> LENGTH: 5
<212> TYPE: PRT
<213> ORGANISM: Artificial Sequence
<220> FEATURE:
<223> OTHER INFORMATION: Peptide linker moiety
<221> NAME/KEY: VARIANT
<222> LOCATION: (0)...(0)
<223> OTHER INFORMATION: Xaa is (GmS)n, where m is
      from 2 to 4 and n is from 1 to 11.

<400> SEQUENCE: 20

Ala Met Xaa Ala Met
 1               5

<210> SEQ ID NO 21
<211> LENGTH: 16
<212> TYPE: PRT
<213> ORGANISM: Drosophila acanthoptera

<400> SEQUENCE: 21

Arg Gln Ile Lys Ile Trp Phe Gln Asn Arg Arg Met Lys Trp Lys Lys
 1               5                  10                  15
```